United States Patent [19]
Chang et al.

[11] Patent Number: 5,919,795
[45] Date of Patent: Jul. 6, 1999

[54] BIPHENYL-2-CARBOXYLIC ACID-TETRAHYDRO-ISOQUINOLIN-6-YL AMIDE DERIVATIVES, THEIR PREPARATION AND THEIR USE AS INHIBITORS OF MICROSOMAL TRIGLYCERIDE TRANSFER PROTEIN AND/OR APOLIPOPROTEIN B (APO B) SECRETION

[75] Inventors: George Chang, Ivoryton; Peter H. Dorff, Norwich; George J. Quallich, North Stonington, all of Conn.

[73] Assignee: Pfizer INc., New York, N.Y.

[21] Appl. No.: 08/952,507

[22] PCT Filed: Jun. 7, 1995

[86] PCT No.: PCT/IB95/00448

§ 371 Date: Nov. 28, 1997

§ 102(e) Date: Nov. 28, 1997

[87] PCT Pub. No.: WO96/40640

PCT Pub. Date: Dec. 19, 1996

[51] Int. Cl.[6] .................. C07D 217/04; C07D 401/06; A61K 31/47; A61K 31/495
[52] U.S. Cl. .......................... 514/310; 546/143
[58] Field of Search ................ 546/143; 514/310

[56] References Cited

U.S. PATENT DOCUMENTS

| | | | |
|---|---|---|---|
| 4,022,900 | 5/1977 | Mathison | 424/258 |
| 5,246,943 | 9/1993 | Blankley et al. | 514/307 |
| 5,350,757 | 9/1994 | Blankley et al. | 514/307 |
| 5,489,686 | 2/1996 | Blankley et al. | 546/147 |
| 5,519,034 | 5/1996 | Kozlik et al. | 514/307 |
| 5,525,614 | 6/1996 | Blankley et al. | 514/307 |
| 5,618,843 | 4/1997 | Fisher et al. | 514/567 |
| 5,731,324 | 3/1998 | Fisher et al. | 514/320 |

FOREIGN PATENT DOCUMENTS

| | | |
|---|---|---|
| 0106140 | 4/1984 | European Pat. Off. . |
| 0635492 | 1/1995 | European Pat. Off. . |
| 0643057 | 3/1995 | European Pat. Off. . |
| 9823593 | 6/1998 | WIPO . |

OTHER PUBLICATIONS

I. W. Mathison et al., Journal of Medicinal Chemistry, 1973, vol. 16, No. 4 pp. 332–336.
Chem. Abstracts vol. 79, No. 5, Abstract No. 79:27073M; 1973.
Chem. Abstracts vol. 84, No. 5, Abstract No. 84:25770Y; 1976.
Mathison, et al., J. Med. Chem. vol. 18, No. 12, pp. 1227–1231, 1975.
Journal Of Medicinal Chemistry, vol. 18, No. 12, Dec. 1975, pp. 1227–1231.

*Primary Examiner*—Zinna Northington Davis
*Attorney, Agent, or Firm*—Peter C. Richardson; Gregg C. Benson; James T. Jones

[57] ABSTRACT

Compounds of formula (I),

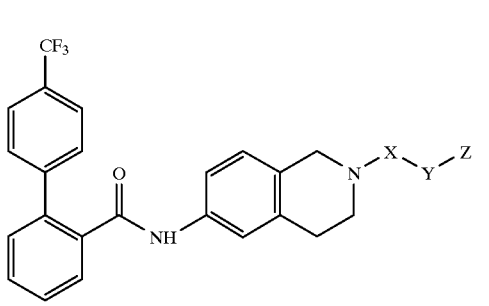

wherin X is $CH_2$, CO, CS or $SO_2$; Y is selected from: a direct link, aliphatic hydrocarbylene radicals having up to 20 carbon atoms, which radical may be mono-substituted by hydroxy, $(C_1-C_{10})$alkoxy, $(C_1-C_{10})$acyl, $(C_1-C_{10})$acyloxy, or $(C_6-C_{10})$aryl, NH, and O, provided that if X is $CH_2$, Y is a direct link; Z is selected from the following groups: (1) H, halo, cyano, (2) hydroxy, $(C_1-C_{10})$alkoxy, $(C_1-C_{10})$alkylthio, $(C_1-C_{10})$acyl, thiophenylcaronyl $(C_1-C_{10})$alkoxycarbonyl, (3) $(C_1-C_{10})$aklkyammo, di$(C_1-C_{10})$alylamino, $(C_6-C_{10})$aryl$(C_1-C_{10})$alkylamino, provided that Y is not O or NH, (4) unsubstituted vinyl, $(C_6-C_{10})$aryl, $(C_3-C_8)$cycloalkyl and fused benz derivatives thereof, $(C_7-C_{10})$polycycloalkyl, $(C_4-C_8)$cycloalkenyl, $(C_7-C_{10})$polycycloalkenyl, (5) $(C_6-C_{10})$aryloxy, $(C_6-C_{10})$aryltio, $(C_6-C_{10})$aryl$(C_1-C_{10})$alkoxy, $(C_6-C_{10})$aryl$(C_1-C_{10})$alkylthio, $(C_3-C_8)$cycloalkyloxy, $(C_4-C_8)$cycloalkenyloxy, (6) heterocyclyl sclected from the group consisting of mono-cyclic radicals and fused polycycuic radicals, wherein said radicals contain a total of from 5 to 14 ring atoms, wherein said radicals contain a total of from 1 to 4 ring heteroatoms independently seloctcd from oxygen, nitrogen, and sulfur, and wherein the individual rings of said radicals may be independendy satated, partally unsaturated, or aromatic, provided that if X is $CH_2$, Z is H or is selected from groups (4) and (6), wherein, when Z contains one or more rings, said rings may each independently bear 0 to 4 substituents independently selected from halo, hydroxy, cyano, nitro, oxo, thioxo, aminosulfonyl, phenyl phenoxy, phenylthio, halophenylthio, benzyl, benzyloxy, $(C_1-C_{10})$alkyl, $(C_1-C_{10})$alkoxy, $(C_1-C_{10})$alkoxycarbonyl, $(C_1-C_{10})$althyltio, $(C_1-C_{10})$altylamino, $(C_1-C_{10})$alkylaminocarbonyl, di$(C_1-C_{10})$alkylamino, di$(C_1-C_{10})$alkylaminocarbonyl, di$(C_1-C_{10})$alkyo$(C_1-C_{10})$alkoxy, $(C_1-C_3)$perfluoroalkyl, $(C_1-C_3)$perfluoroalkoxy, $(C_1-C_{10})$acyl, $(C_1-C_{10})$acyloxy, $(C_1-C_{10})$acyloxy$(C_1-C_{10})$alkyl, and pyrrolidinyl; and pharmaceutically acceptable salts thereof.

36 Claims, No Drawings

BIPHENYL-2-CARBOXYLIC ACID-TETRAHYDRO-ISOQUINOLIN-6-YL AMIDE DERIVATIVES, THEIR PREPARATION AND THEIR USE AS INHIBITORS OF MICROSOMAL TRIGLYCERIDE TRANSFER PROTEIN AND/OR APOLIPOPROTEIN B (APO B) SECRETION

This is a National Phase filing under 35 U.S.C. §371 based on PCT/IB95/00448, which was filed internationally on Jun. 7, 1995.

FIELD OF THE INVENTION

This invention relates to compounds which are inhibitors of microsomal triglyceride transfer protein and/or apolipoprotein B (Apo B) secretion, and which are accordingly useful for the prevention and treatment of atherosclerosis and its clinical sequelae, for lowering serum lipids, and related diseases. The invention further relates to compositions comprising the compounds and to methods of treating atherosclerosis, obesity, and related diseases and/or conditions with the compounds.

BACKGROUND OF THE INVENTION

Microsomal triglyceride transfer protein (MTP) catalyzes the transport of triglyceride, cholesteryl ester, and phospholipids. It has been implicated as a probable agent in the assembly of Apo B-containing lipoproteins, biomolecules which contribute to the formation of atherosclerotic lesions. See European Patent application publication no. 0 643 057 A1, European Patent application publication no. 0 584 446 A2, and Wetterau et al., Science, 258, 999–1001, (1992). Compounds which inhibit MTP and/or otherwise inhibit Apo B secretion are accordingly useful in the treatment of atherosclerosis. Such compounds are also useful In the treatment of other diseases or conditions in which, by inhibiting MTP and/or Apo B secretion, serum cholesterol and triglyceride levels can be reduced. Such conditions include hypercholesterolemia, hypertriglyceridemia, pancreatits, and obesity; and hypercholesterolemia, hypertriglyceridemia, and hyperlipidemla associated with pancreatitis, obesity, and diabetes.

Examples of general information and/or documents defining the general state of the art include EP-A-0 635 492, J. Med. Chem. (1975) 18(12), 1227–1231, U.S. Pat. No. 4,022,900, and EP-A-0 106 140.

SUMMARY OF THE INVENTION

This invention provides compounds of formula I

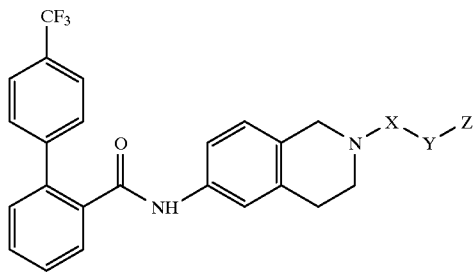

wherein
X is $CH_2$, CO, CS, or $SO_2$;
Y is selected from:

a direct link (i.e., a covalent bond),
aliphatic hydrocarbylene radicals having up to 20 carbon atoms, which radical may be mono-substed by hydroxy, $(C_1-C_{10})$alkoxy, $(C_1-C_{10})$acyl, $(C_1-C_{10})$acyloxy, or $(C_6-C_{10})$aryl,
NH, and O, provided that if X is $CH_2$, Y is a direct link;
Z is selected from the following groups:
(1) H, halo, cyano,
(2) hydroxy, $(C_1-C_{10})$alkoxy, $(C_1-C_{10})$alkylthio, $(C_1-C_{10})$acyl, thiophenylcarbonyl, $(C_1-C_{10})$alkylcarbonyl,
(3) $(C_1-C_{10})$alkylamino, di$(C_1-C_{10})$alkylamino, $(C_6-C_{10})$aryl$(C_1-C_{10})$alkylamino, provided that Y is not O or NH,
(4) unsubstituted vinyl, $(C_6-C_{10})$aryl, $(C_3-C_8)$cycloalkyl and fused benz derivatives thereof, $(C_7-C_{10})$polycycloalkyl, $(C_4-C_8)$cycloalkenyl, $(C_7-C_{10})$polycycloalkenyl,
(5) $(C_6-C_{10})$aryloxy, $(C_6-C_{10})$arylthio, $(C_6-C_{10})$aryl$(C_1-C_{10})$alkoxy, $(C_6-C_{10})$aryl$(C_1-C_{10})$alkylthio, $(C_3-C_8)$cycloalkyloxy, $(C_4-C_8)$cycloalkenyloxy,
(6) heterocyclyl selected from the group consisting of monocyclic radicals and fused polycyclic radicals, wherein said radicals contain a total of from 5 to 14 ring atoms, wherein said radicals contain a total of from 1 to 4 ring heteroatoms independently selected from oxygen, nitrogen, and sulfur, and wherein the individual rings of said radicals may be independently saturated, partially unsaturated, or aromatic,
provided that if X is $CH_2$, Z is H or is selected from groups (4) and (6),
wherein, when Z contains one or more rings, said rings may each independently bear 0 to 4 substituents independently selected from halo, hydroxy, cyano, nitro, oxo (O=), thioxo(S=), aminosulfonyl, phenyl, phenoxy, phenylthio, halophenylthio, benzyl, benzyloxy, $(C_1-C_{10})$alkyl, $(C_1-C_{10})$alkoxy, $(C_1-C_{10})$alkoxycarbonyl, $(C_1-C_{10})$alkylthio, $(C_1-C_{10})$alkylamino, $(C_1-C_{10})$alkylaminocarbonyl, di$(C_1-C_{10})$alkylamino, di$(C_1-C_{10})$alkylaminocarbonyl, di$(C_1-C_{10})$alkylamino $(C_1-C_{10})$alkoxy, $(C_1-C_3)$perfluoroalkyl, $(C_1-C_3)$perfluoroalkoxy, $(C_1-C_{10})$acyl, $(C_1-C_{10})$acyloxy, $(C_1-C_{10})$acyloxy$(C_1-C_{10})$alkyl, and pyrrolidinyl;
and pharmaceutically acceptable salts thereof.

Reference to Z as "heterocyclyl" means any single ring or fused ring system containing at least one ring heteroatom independently selected from O, N, and S. Thus a polycyclic fused ring system containing one or more carbocyclic fused saturated, partially unsaturated, or aromatic rings (usually benz rings) is within the definition of heterocyclyl so long as the system also contains at least one fused ring which contains at least one of the aforementioned heteroatoms. As a substituent, such heterocyclyls may be attached to the remainder of the molecule from either a carbocyclic (e.g., benz) ring or from a heterocyclic ring.

Reference to Z containing "one or more rings" is intended to mean any (single or fused) cyclic moiety or moieties contained in Z. The rings may be carbocyclic or heterocyclic, saturated or partially unsaturated, and aromatic or non-aromatic.

Reference to a fused polycyclic ring system or radical means that all rings in the system are fused.

Reference to "halo" in this specification is inclusive of fluoro, chloro, bromo, and iodo unless noted otherwise.

Reference to an "aryl" substitutent (e.g. $(C_6-C_{10})$aryl) means the ring or substitutent is carbocyclic. Aromatic moieties which contain 1 or more heteroatoms are included as a subset of the term "heterocyclyl", as discussed above.

Reference to an "acyl" substituent refers to an alphatic or cyclic hydrocarbon moiety attached to a carbonyl group through which the substituent bonds.

Reference to "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The central benz-heterocyclic ring system of formula I, i.e., the fused bicyclic ring system attached through its single ring nitrogen to —XYZ, is referred to herein as a "1,2,3,4-tetrahydroisoquinoline" for convenience, and this is the convention used most frequently when naming compounds according to the invention as 2-substituted 1,2,3,4-tetrahydroisoquinolin-6-yl amides. It is noted that less frequently, when named as a substituent in a compound, this central ring system is also denoted as a 6-substituted "3,4,-dihydro-1H-isoqulnolin-2-yl" moiety.

A subgroup of compounds of formula I as defined above includes those wherein:

X is $CH_2$, CO, or $SO_2$;
Y is selected from:
 a direct link, NH,
 $(C_1-C_{10})$alkyiene and $(C_2-C_{10})$alkenylene, either of which may be substituted with phenyl,
provided that X is $CH_2$, Y is a direct link,
Z is selected from the following groups:
 (1) H,
 (2) $(C_1-C_{10})$alkoxy, $(C_1-C_{10})$alkylthio,
 (3) $(C_1-C_{10})$alkylamino, di$(C_1-C_{10})$alkylamino, $(C_6-C_{10})$aryl$(C_1-C_{10})$alkylamino, provided that Y is not NH,
 (4) unsubstituted vinyl, $(C_6-C_{10})$aryl, $(C_3-C_8)$cycloalkyl, $(C_4-C_8)$cycloalkenyl,
 (5) $(C_6-C_{10})$aryloxy,
 (6) heterocyclyl selected from the group consisting of five- and six-membered heterocyclic radicals, which may be saturated, partially unsaturated, or aromatic, and the fused benz derivatives thereof, wherein said radicals may contain a total of from 1 to 3 ring heteroatoms independently selected from oxygen, nitrogen, and sulfur,
 provided that if X is $CH_2$, Z is selected from groups (4) and (6)
 wherein, when Z contains one or more rings, said rings may each independently bear 0 to 3 substituents independently selected from halo, hydroxy, nitro, $(C_1-C_8)$alkyl, $(C_1-C_6)$alkoxy; di$(C_1-C_6)$alkylaminocarbonyl, $(C_1-C_3)$perfluoroalkoxy, $(C_1-C_{10})$acyl, and $(C_1-C_{10})$acyloxy,
 and pharmaceutically acceptable salts thereof.

A more particular subgroup includes those compounds within the above subgroup wherein X is methylene, Y is a direct link, and Z is selected from $(C_6-C_{10})$aryl, $(C_3-C_8)$cycloalkyl, and $(C_4-C_8)$cycloalkenyl each of which may bear 0 to 3 of the independent substituents noted for Z in the above subgroup, unsubstituted vinyl, and pharmaceutically acceptable salts thereof. Specific values for each include the illustrative values for each given hereinafter.

Another more particular subgroup includes those compounds within the above subgroup wherein X is methylene or CO, Y is a direct link, and Z is heterocyclyl selected from thiophenyl, pyrrolidinyl, pyrrolyl, furanyl, thiazolyl, isoxazolyl, imidazolyl, 1,2,4-triazolyl, pyridyl, pyrimidinyl, and the fused bicyclic (ortho) benz derivatives thereof, including benzimidazolyl, benzthiazolyl, indolyl, isoindolyl, benzofuranyl, benzothiophenyl, benzthiazolyl, quinolinyl, isoquinolinyl, and quinazolinyl, each of which may bear 0 to 3 of the independent substituents noted for Z in the above subgroup, and pharmaceutically acceptable salts thereof.

Specific values for Z as heterocyclyl which may bear 0–3 independent substituents noted for Z in the above subgroup include 2-, and 3-thiophenyl; 2- and 3-benzo[b]thiophenyl: 1-, 2- and 4-imidazolyl; 2-benzimidazolyl; 2-, 4-, and 5-thiazolyl; 2-benzothiazolyl; 3-, 4-, and 5-isoxazolyl; 2-quinoxalinyl; 1-, 2-, and 3-pyrrolidinyl; 2-, 3-, and 4-pyridyl; 2- and 4-pyrimidinyl; 2-, 3-, and 4-quinolinyl; 1-, 3-, and 4-isoquinoline; 1-, 2-, and 3-indolyl; 1-, 2-, and 3-isoindolyl; 2- and 3-tetrahydrofuranyl; 1-, 2-, and 3-pyrrolyl; 2- and 3-furanyl; 2- and 3-benzo[b]furanyl; 1-, 3-, and 4-pyrazolyl; and 1,2,4-triazolyl-3-yl.

A preferred group of compounds includes those compounds wherein
 X is $CH_2$ or CO;
 Y is a direct link;
 Z is
  H, unsubstituted vinyl, phenyl,
  imidazolyl, thiazolyl, thiophenyl, 1,2,4triazolyi, pyridinyl, and pyrimidinyl each of which may bear 0 to 3 of the independent substituents previously noted for the above subgroup;
 and pharmaceutically acceptable salts thereof. Specific values of Z (as heterocycyl) for this preferred group include the corresponding specific values noted above.

Within the above preferred group, a subgroup includes those compounds wherein X is CO.

Within the above preferred group, a second subgroup includes those compounds wherein X is $CH_2$.

The invention further provides a pharmaceutical composition suitable for the treatment of conditions including atherosclerosis, pancreatits, obesity, hypercholesterolemia, hypertriglyceridemia, hyperlipidemia, and diabetes, comprising a compound of formula I as hereinbefore defined, and a pharmaceutically acceptable carrier.

The compounds of this invention inhibit or decrease apo B secretion, likely by the inhibition of MTP, although it may be possible that other mechanisms are involved as well. The compounds are useful in any of the diseases or conditions in which apo B, serum cholesterol, and/or triglyceride levels are elevated. Accordingly, the invention further provides a method of treating a condition selected from atherosclerosis, pancreatitis, obesity, hypercholesteremia, hypertriglyceridemia, hyperlipidemia, and diabetes, comprising administering to a mammal, especially a human, in need of such treatment an amount of a compound of formula I as defined above sufficient to decrease the secretion of apolipoprotein B. A subgroup of the preceding conditions includes atherosclerosis, obesity, pancreatitis, and diabetes. A more particular subgroup includes atherosclerosis.

The term "treating" as used herein includes preventative as well as disease remitative treatment.

The invention further provides a method of decreasing apo B secretion in a mammal, especially a human, comprising administering to said mammal an apo B-(secretion) decreasing amount of a compound of formula I as defined above.

Certain intermediates are additionally provided as a further feature of the invention:

4'-trifluoromethyl-biphenyl-2-carboxylic acid(1,2,3,4-tetrahydro-isoquinolin-6-yl)-amide, 4'-triuoromethyl-biphenyl-2-carboxylic acid-[3-(2-hydroethyl)-4-hydroxylmethyl-phenyl]-amide, 2-(2-hydroxymethyl-5-nitro-phenyl)-ethanol, 6-nitro-3,4-dihydro-1H-isoquinoline-2-arboxylic acid tert-butyl ester, 6amino-3,4-dihydro-1H-isoquinoline-2-carboxylic acid tert-butyl ester, and 2-(5-amino-2-hydroxymethyl-phenyl)-ethanol.

It will be appreciated by those skilled in the art that certain compounds of formula I contain an asymmetrically substituted carbon atom and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of atherosclerosis, obesity, and the other conditions noted herein, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of the conditions noted herein by the standard tests described hereinafter.

The chemist of ordinary skill will recognize that certain combinations of substituents or moieties listed in this invention define compounds which will be less stable under physiological conditions (e.g., those containing aminal or acetal linkages). Accordingly, such compounds are less preferred.

An "aliphatic hydrocarbylene radical" for purposes of this invention means a divalent open-chain organic radical containing carbon and hydrogen only. The radical serves as a linking group, denoted above as Y. The radical may be straight chain or branched and/or saturated or unsaturated, containing up to three unsaturated bonds, either double, triple or a mixture of double and triple. The two valences may be on different carbon atoms or on the same carbon atom, and thus the term "alkylidene" is subsumed under this definition. The radical will typically be classified as a $(C_1–C_{20})$alkylene radical, a $(C_2–C_{20})$alkenylene radical, or a $(C_2–C_{20})$alkynylene radical. Typically the radical will contain 1–10 carbon atoms, although longer chains are certainly feasible and within the scope of this invention, as demonstrated in the Examples.

Alkylene radicals include those saturated hydrocarbon groups having 1–20, preferably 1–10 carbon atoms, desived by removing two hydrogen atom from a corresponding saturated acyclic hydrocarbon. Illustrative values having 1–10 carbon atoms include straight chain radicals having the formula $(CH_2)_n$ wherein n is 1 to 10, such as methylene, dimetnylene, trimethylene, tetramethylene, pentamethylene, hexamethylene, heptamethylene, octamethylene, nonamethylene and so forth. Also included are alkylidene radicals such as ethylidene, propylidene, butylidene, and sec-butylidene. Also included are branched isomers such as 1,1-dimethyidimethylene, 1,1-dimethyltetramethylene, 2,2-dimethytrimethylene and 3,3-dimethylpentamethylene.

Alkenylene radicals include those straight or branched chain radicals having 2–20 carbon atoms, preferably 2–10 carbon atoms, derived by removal of two hydrogen atoms from a corresponding acyclic hydrocarbon group containing at least one double bond. Illustrative values for alkenylene radicals having one double bond include ethenylene (vinylene), propenylene, 1-butenylene, 2-butenylene, and isobutenylene. Alkenylene radicals containing two double bonds (sometimes referred to in the art as alkadienylene radicals) include 3-methyl-2,6heptadienylene, 2-methyl-2,4-heptadienylene,2,8-nonadienylene,3-methyl-2,6-octadienylene,and2,6-decadienylene. An illustrative value for an alkylene radical containing three double bonds (an alkatrienylene radical) is 9,11,13-heptadecatrienylene.

Alkynylene radicals include those straight or branched chain radicals having 2–20 carbon atoms, preferably 2–10 carbon atoms, derived by removal of two hydrogen atoms from a corresponding acyclic hydrocarbon group containing at least one triple bond. Illustrative values include ethynylene, propynylene, 1-butynylene, 1-pentynylene, 1-hexynylene, 2-butynylene, 2-pentynylene, 3,3-dimethyl-1-butynylene, and so forth.

Following are illustrative values for other moieties and substituents named above, which are not to be taken as limiting. It is noted that throughout the specification, if a cyclic or polycyclic radical which can be bonded through different ring atoms is referred to without noting a specific point of attachment, all possible points are intended, whether through a carbon atom or a trivalent nitrogen. As examples, reference to (unsubstituLed) "naphthyl" means naphth-1-yl and naphth2-yl; reference to "pyridyl" means 2-, 3-, or 4-pyridyl; reference to "indolyl" means attachment or bonding through any of the 1-, 2-, 3-, 4-, 5-, 6-, or 7- positions.

Illustrative values for $(C_1–C_{10})$alkoxy include methoxy, ethoxy, propoxy, isopropoxy, butoxy, isobutoxy, pentoxy, hexoxy, heptoxy, and so forth.

Illustrative values for $(C_1–C_{10})$alkylthio include the corresponding sulfur-containing compounds of $(C_1–C_{10})$alkoxy listed above, including methylthio, ethylthio, propylthio, isopropylthio, butylthio, isobutylthio, pentylthio, hexylthio, heptylthio, and so forth.

Illustrative values for $(C_1–C_{10})$acyl include values for $(C_1–C_{10})$alkanoyl such as formyl, acetyl, propionyl, butyryl, and isobutyryl. Also included are other common cycle-containing radicals such as benzoyl.

Illustrative values for $(C_1–C_{10})$acyloxy include values for $(C_1–C_{10})$alkanoyloxy such as formyloxy, acetyloxy, propionyloxy, butyryloxy, and isobutyryloxy. Also included are other common cycle-containing radicals such as benzoyloxy.

Illustrative values for $(C_1–C_{10})$alkoxycarbonyl include methoxycarbonyl, ethoxycarbonyl, propoxycarbonyl, isopropoxycarbonyl, butoxycarbonyl, and isobutoxycarbonyl.

Illustrative values for $(C_1–C_{10})$alkylamino include methylamino, ethylamino, propylamino, isopropylamino, butylamino, and isobutylamino.

Illustrative values for di-$(C_1–C_{10})$alkylamino include dimethylamino, diethylamino, dipropylamino, dibutylamino, and diisobutylamino.

Illustrative values for $(C_6–C_{10})$aryl$(C_1–C_{10})$alkylamino are benzylamino, (1-phenylethyl)amino, and (2-phenylethyl)amino;

Illustrative values for $(C_6–C_{10})$aryl include phenyl and naphthyl.

Illustrative values of $(C_3–C_8)$cycloalkyl include cyclopropyl, cyclobutyl, cyclopentyl, cyclohexyl, and cycloheptyl.

Illustrative values for fused benz derivatives of $(C_3–C_8)$ cycloalkyl include 1,2,3,4-tetrahydronaphthalenyl, indanyl, and fluorenyl.

Illustrative values of polycycloalkyl include adamantyl and 2-bicyclo[2.2.1]heptyl.

Illustrative values for $(C_4–C_8)$cycloalkenyl include cyclobutenyl, cyclopentyenyl, cyclohexenyl, and cycloheptenyl.

Illustrative values for polycycloalkenyl include bicyclo [3.1.1]hept-2-enyl.

Illustrative values for $(C_6-C_{10})$aryloxy include phenoxy and naphthyloxy.

Illustrative values for $(C_6-C_{10})$arylthio include phenythio and naphthylthio.

Illustrative values for $(C_6-C_{10})$aryl$(C_1-C_{10})$alkoxy include benzyloxy and phenylethoxy.

Illustrative values for $(C_6-C_{10})$aryl$(C_1-C_{10})$alkyithio include benzylthio and phenylethylthio.

Illustrative values for $(C_3-C_8)$cycloalkyloxy include cyclopropyloxy, cyclobutyloxy, cyclopentyloxy, cyclohexyloxy, and cycloheptyloxy.

Illustrative values for $(C_4-C_8)$cycloalkenyloxy include cyclobutenyloxy, cyclopentenyloxy, cyclohexenyloxy, and cycloheptenyloxy.

Illustrative values for heterocyclyl substituents which are five-member monocyclic radicals include furanyl, thiophenyl, pyrrolyl, pyrrolidinyl, oxazolyl, thiazolyl, imidazolyl, pyrazolyl, isoxazolyl, isothiazolyl, 1,2,3-triazolyl, 1,2,4-traizolyl, and 1,3,4thiadiazolyl, and the like.

Illustrative values for heterocyclyl substituents which are six-membered monocyclic radicals include 2H- and 4H-pyranyl, pyridyl, piperidinyl, piperazinyl, pyridazinyl, pyrimidinyl, pyrazinyl, morpholinyl, thiomorpholinyl, 1,3,5-triazinyl, and the like.

Illustrative values for heterocyclyl substituerts which are fused benz derivatives of five-membered heterocyclic radicals include indolyl, isoindolyl, indolinyl, benzofuranyl, benzothiophenyl, benzimidazolyl, benzthiazolyl, and carbazolyl.

Illustrative values for heterocyclyl substituents which are fused benz derivatives of six-membered heterocyclic radicals include quinolinyl, isoquinolinyl, quinazolinyl, phthalazinyl, phenothiazinyl, acridinyl, and phenoxazinyl.

Illustrative examples for heterocyclyl groups which are fused polycyclic radicals other than the fused benz systems exemplified above include purinyl and pteridinyl.

Illustrative values of $(C_1-C_{10})$alkyl include methyl, ethyl, propyl, isopropyl, isobutyl, butyl, tertbutyl, pentyl, hexyl, and the like.

Illustrative values for $(C_1-C_3)$perfluoroalkyl include trifluoromethyl, pentafluoroethyl, and heptafluoropropyl.

Illustrative values for $(C_1-C_3)$perfluoroalkoxy include trifluoromethoxy and pentafluoroethoxy.

Compounds according to the invention can frequently be categorized into groups based on the linking group formed by the ring nitrogen of the 1,2,3,4-tetrahydroisoquinoline ring (shown in formula I) taken together with the group in -XYZ which links the XYZ moiety to the said ring nitrogen. Such categories include

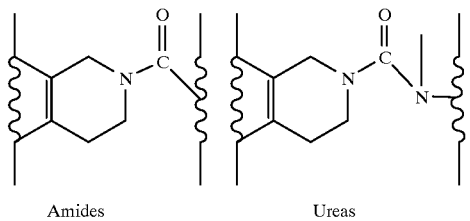

Amides                    Ureas

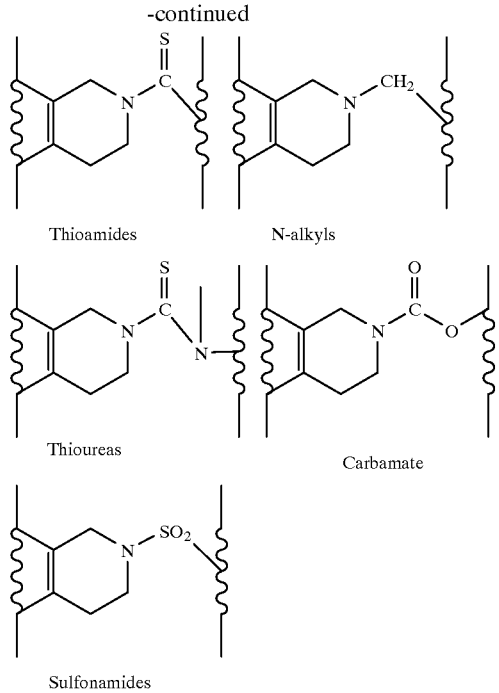

Thioamides          N-alkyls

Thioureas           Carbamate

Sulfonamides

Referring to the above linking groups as illustrated, for amides and thioamides (X=CO or CS, respectively) Y is preferably a direct link or hydrocarbylene. In these compounds wherein Y is a direct link, bonding is preferably through the carbonyl or thiocarbonyl group to an aliphatic (i.e., open chain) carbon atom in Z. The said aliphatic carbon atom can be part of a chain which contains one or more heteroatoms. Bonding can also preferably be through the carbonyl or thiocarbonyl group to a cyclic carbon atom. By "cyclic carbon atom" is meant a saturated or unsaturated carbon atom contained in a (saturated, partially unsaturated, or aromatic) carbocyclic or heterocyclic ring. For compounds wherein Y is hydrocarbylene, bonding is through the carbonyl or thiocarbonyl group to an aliphatic carbon atom in Y.

For ureas and thioureas wherein X=CO or CS, respectively and Y=NH, bonding is preferably through the (easternmost as shown) amino group to a cyclic carbon atom in Z. For some ureas and thioureas (X=CO, Y=direct bond) the (easternmost) amino nitrogen is part of Z. In this case bonding is preferably through the easternmost amino group to an aliphatic carbon atom in the remaining portion of Z.

For sulfonamides according to the invention X=SO$_2$ and Y is preferably hydrocarbylene, or a direct link. For sulfonamides wherein Y is hydrocarbylene, bonding is through the sulfonyl group to an aliphatic carbon atom in Y. For sulfonamides wherein Y is a direct link, bonding is preferably through the sulfonyl group to a cyclic carbon atom in Z. For sulfonamides wherein Y is a direct link, bonding can also be to NH which is part of Z, in which case bonding is through X directly to an amino nitrogen in Z.

N-alkyls (X=CH$_2$, Y=direct link) preferably bond through the methylene group to a cyclic carbon atom in Z.

For carbamates wherein X=CO and Y=O bonding is preferably through the oxy (O) portion of the linkage to a cyclic carbon atom in the remaining portion of Z. For carbamates wherein X=CO and Y=direct link the oxy linkage is part of Z, and in these bonding is preferably to a cyclic or aliphalic carbon atom In the remaining portion of Z, most preferably to an aliphatic carbon atom in the remaining portion of Z.

For those compounds of formula I wherein Y is hydrocarbylene, bonding to Z is through an aliphatic carbon atom in Y preferably to H or to a cyclic carbon atom or a heteroatom in Z.

When grouping compounds below and in the Examples, it is the above structural categories to which reference is made.

Preferred compounds include the following which, where possible, have been categorized according to the types of linking groups shown in partial structure above.

AMIDES

4'-Trifluoromethyl-biphenyl-2-carboxylic acid (2-phenyl-acetyl-1,2,3,4-tetrahydroisoquinolin-6-yl)-amide 4'-Trifluoromethyl-biphenyl-2-carboxylic acid (2-phenoxy-acetyl-1,2,3,4-tetrahydroisoquinotin-6-yl)-amide 4'-Trifluoromethyl-biphenyt2carboxylic acid (2-pentanoyl-1,2,3,4tetrahydroisoquinolin-6-yl)-amide 4'-Trifiuoromethyl-biphenyl-2 carboxylic acid (2-cyclobutane carbonyl-1,2,3,4-tetrahydroisoquinolin-6-yl)-amide 4'-Trifluoromethyl-biphenyl-2-caboxylic acid [2-(thiophen-2-yl-acetyl)-1,2,3,4-tetrahydroisoquinolin-6-yl]-amide 4'-Trifluoromethyl-biphenyl-2-carboxylic acid (2-butyryl-1,2,3,4tetrahydrnisoquinolin-6-yl)-amide 4'-Trifluoromethyl-biphenyl-2-carboxylic acid (2-ethoxy-acetyl-1,2,3,4-tetrahydroisoquinolin-6-yl)-amide 4'-Trifluoromethyl-biphenyl-2-carboxylic acid {2-[(4fluoro-phenyl)-acetyl-]-1,2,3,4-tetrahydroisoquinolin-6-yl}-amide 4'-Trifluoromethyl-biphenyl-2-carboxylic acid [2-(3-methyl-butyryl)-1,2,3,4-tetrahydroisoquinolin-6yl]-amide 4'-Trifluoromethyl-biphenyl-2-carboxylic acid (2-but-3-enoyl-1,2,3,4-tetrahydroisoquinolin-6-yl)-amide 4'-Trifluoromethyl-biphenyl-2-carboxylic acid (2-methoxy-acetyl-1,2,3,4tetrahydroisoquinolin-6-yl)-amide 4'-Trifluoromethyl-biphenyl-2-carboxylic acid (2-ethylthio-acetyl-1,2,3,4tetrahydroisoquinolin-6-yl)-amide 4'-Trifluoromethyl-biphenyl-2-carboxylic acid [2-(6diethyl-carbamoyl-cyclohex-3-enecarbonyl)-1,2,3,4-tetrahydroisoquinolin-6-yl]-amide 4'-Trifluoromethyl-biphenyl-2-caboxylic acid [2-(cyclopent-1-enyl-acetyl)-1,2,3,4-tetrahydroisoquinolin-6-yl]-amide 4'-Trifluoromethyl-biphenyl-2-carboxylic acid (2-hex-3enoyl-1,2,3,4-tetrahydroisoquinolin-6-yl)-amide 4'-Trifluoromethyl-biphenyl-2-carboxylic acid [2-(tetrahydrofuran-3-carbonyl)-1,2,3,4-tetrahydroisoquinolin-6-yl]-amide 4'-Trifluoromethyl-biphenyl-2-carboxylic acid [2-(thiophen-3-yl-acetyl)-1,2,3,4-tetrahydroisoquinolin-6-yl]-amide 4'-Trifluoromethyl-biphenyl-2-carboxylic acid [2-(pyridine-2-carbonyl)-1,2,3,4-tetrahydroisoquinolin-6-yl]-amide

UREAS

6-[(4'-Trifluoromethyl-biphenyl-2-carbonyl)-amino]-3,4-dihydro-1H-isoquinoline-2-carboxylic acid phenylamide 6-[(4'-Trifluoromethyl-biphenyl-2-carbonyl)-amino]-3,4-dihydro-1H-isoquinoline-2-carboxylic acid hexylamide 6-[(4'-Trifluoromethyl-biphenyl-2-carbonyl)-amino]-3,4-dihydro-1H-isoquinoline-2-carboxylic acid benzylamide 6-[(4'-Trifluoromethyl-biphenyl-2-carbonyl)-amino]-3,4-dihydro-1H-isoquinoline-2-carboxylic acid [(R)-1-phenyl-ethyl]-amide 6-[(4'-Trifluoromethyl-biphenyl-2-carbonyl)-amino]-3,4-dihydro-1H-isoquinoline-2-carboxylic acid pyridin-2-ylamide

SULFONAMIDES

4'-Trifluoromethyl-biphenyl-2-carboxylic acid [2-(propane-2-sufonyl)-1,2,3,4tetrahydroisoquinolin-6-yl]-amide 4'-Trifluoromethyl-biphenyl-2-carboxylic acid (2-dimethylsulfamoyl-1,2,3,4-tetrahydroisoquinolin-6-yl)-amide 4'-Trifluoromethyl-biphenyl-2-carboxylic acid [2-(2-trifluoromethoxy-benzenesulfonyl)-1,2,3,4tetrahydroisoquinolin-6-yl]-amide

THIOUREAS

4'-Trifluoromethyl-biphenyl-2-carboxylic acid (2-cyclopropylthiocarbamoyl-1,2,3,4-tetrahydroisoquinolin-6-yl)-amide

N-ALKYLS

4'-Trifluoromethyl-biphenyl-2-carboxylic acid [2-(2,6,6-trimethyl-cyclohex-2-enylmethyl)-1,2,3,4tetrahydroisoquinolin-6-yl]-amide 4'-Trifluoromethyl-biphenyl-2-carboxylic acid [2-(2,4-dichloro-benzyl)-1,2,3,4tetrahydroisoquinolin-6-yl]-amide 4'-Trifluoromethyl-biphenyl-2-carboxylic acid [2-(1,5a,6,9,9a,9b-hexahydro-4H-dibenzofuran-4a-ylmethyl)-1,2,3,4-tetrahydroisoquinolin-6-yl]-amide 4'-Trifluoromethyl-biphenyl-2-carboxylic acid (2-thiophen-2-ylmethyl-1,2,3,4tetrahydroisoquinolin-6-yl)-amide 4'-Trifluoromethyl-biphenyl-2-carboxylic acid [2-(1H-pyrrol-2-ylmethyl)-1,2,3,4-tetrahydroisoquinolin-6-yl]-amide 4'-Trifluoromethyl-biphenyl-2-carboxylic acid (2-furan-2-ylmethyl-1,2,3,4tetrahydroisoquinolin-6-yl)-amide Acetic acid 5-{6-[(4'-trifluoromethyl-biphenyl-2-carbonyl)-amino]-3,4-dihydro-1H-isoquinolin-2-ylmethyl}-furan-2-ylmethyl ester 4'-Trifluoromethyl-biphenyl-2-carboxylic acid (2-thiophen-3-ylmethyl-1,2,3,4-tetrahydroisoquinolin-6-yl)-amide 4'-Trifluoromethyl-biphenyl-2-carboxylic acid [2-(2,5-dimethoxy-tetrahydrofuran-3-ylmethyl)-1,2,3,4-tetrahydro-isoquinolin-6-yl]-amide 4'-Trifluoromethyl-biphenyl-2-carboxylic acid (2-benzyl-1,2,3,4-tetrahydroisoquinolin-6-yl)-amide 4'-Trifluoromethyl-biphenyl-2-carboxylic acid (2-pyridin-2-ylmethyl-1,2,3,4-tetrahydroisoquinolin-6-yl)-amide 4'-Trifluoromethyl-biphenyl-2-carboxylic acid (2-quinolin-2-ylmethyl-1,2,3,4tetrahydroisoquinolin-6-yl)-amide 4'-Trifluoromethyl-biphenyl-2-carboxylic acid [2-(3-chloro-benzyl)-1,2,3,4-tetrahydroisoquinolin-6-yl]-amide 4'-Trifluoromethyl-biphenyl-2-carboxylic acid (2-pyrimidin-2-ylmethyl-1,2,3,4-tetrahydroisoquinolin-6-yl)-amide 4'-Trifluoromethyl-biphenyl-2-carboxylic acid [2-(3-nitro-benzyl)-1,2,3,4-tetrahydroisoquinolin-6-yl]-amide 4'-Trifluoromethyl-biphenyl-2-carboxylic acid [2-(1H-imidazol-2-ylmethyl)-1,2,3,4-tetrahydroisoquinolin-6-yl]-amide 4'-Trifluoromethyl-biphenyl-2-carboxylic acid [2-(1-methyl-pyrrol-2-ylmethyl)-1,2,3,4-tetrahydroisoquinolin-6-yl]-amide 4'-Trifluoromethyl-biphenyl-2-carboxylic acid [2-(1H-benzoimidazol-2-ylmethyl)-1,2,3,4-tetrahydroisoquinolin-6-yl]-amide 4'-Trifluoromethyl-biphenyl-2-carboxylic acid (2-thiazol-2-ylmethyl-1,2,3,4-tetrahydroisoquinolin-6-yl)-amide 4'-Trifluoromethyl-biphenyl-2-carboxylic acid [2-(1-methyl-imidazol-2-ylmethyl)-1,2,3,4-tetrahydro-isoquinolin-6-yl]-amide 4'-Trifluoromethyl-biphenyl-2-carboxylic acid [2-(1H-[1,2,4]triazol-3-ylmethyl)-1,2,3,4-tetrahydro-isoquinolin-6-yl]-amide 4-trifluoromethyl-biphenyl-2-carboxylic acid [(2-allyl)-1,2,3,4-tetrahydroisoquinoline-6-yl]amide

CARBAMATES

6-[(4'-Trifluoromethyl-biphenyl-2-carbonyl)-amino]-3,4-dihydro-1H-isoquinoline-2-carboxylic acid tert-butyl ester Particularly preferred compounds include the following:

4-Trifluoromethyl-biphenyl-2-carboxylicacid[2-(thiophen-2-yl-acetyl)-1,2,3,4tetrahydroisoquinolin-6-yl]-amide, 6-[(4'-Trifluoromethyl-biphenyl-2-carbonyl)-amino]-3,4-dihydro-1H-isoquinoline-2-carboxylic acid (1-phenyl-ethyl)-amide, 4'-Trifluoromethyl-biphenyl-2-carboxylic acid (2-pyridin-2-ylmethyl-1,2,3,4-tetrahydroisoquinolin-6-yl)-amide, 4'-Trifluoromethyl-biphenyl-2-carboxylic acid [2-(1H-imidazol-2-ylmethyl)-1,2,3,4-tetrahydro-isoquinolin-6-yl]-amide, 4'-Trifluoromethyl-biphenyl-2-carboxylic acid (2-thiazol-2-ylmethyl-1,2,3,4tetrahydroisoquinolin-6-yl)-amide, and 4'-Trifluoromethyl-biphenyl-2-carboxylic acid [2-(1H-[1,2,4]triazol-3-ylmethyl)-1,2,3,4-tetrahydro-isoquinolin-6-yl]-amide,

DETAILED DESCRIPTION

In the discussion which follows, common chemical abbreviations and acronyms have been employed: Me (methyl); Et (ethyl); THF (tetrahydrofuran); BOC (tertbutyloxycarbonyl, a blocking group); Ms (methanesulfonyl, mesyl); TFA (trifluoroacetic acid); Ac (Acetyl); RP (reverse phase); HPLC (high performance liquid chromatography);

Compounds of formula I can be made by processes which include processes known in the chemical arts for the production of similar compounds. Such processes for the manufacture of a compound of formula I as defined above are provided as further features of the invention and are illustrated by the following procedures in which the meanings of generic radicals are as given above unless otherwise qualified. The processes involve treating a compound of formula II,

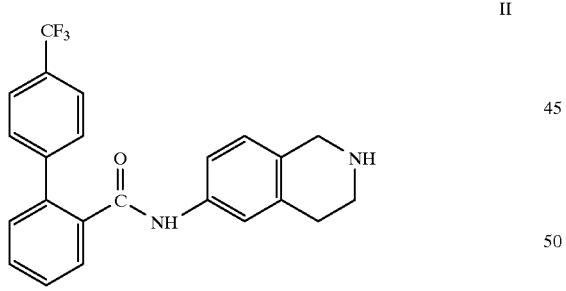

II which contributes the western portion of the molecule (i.e., the moiety consisting of formula II with the hydrogen removed from the tetrahydroisoquinolinyl ring nitrogen) with a reactant which adds the eastern (XYZ) moiety. Reactants which furnish the eastern moiety are generally commercially available or well precedented in the scientific literature. The compound of formula II is 4'-trifluoromethylbiphenyl-2-carboxylic acid (1,2,3,4-tetrahydroisoquinolin-6-yl)amide and is referred to herein simply as "compound II" for the sake of convenience. The western portion of the molecule it contributes to compounds according to the invention is the 6-[(4'-trifluoromethyl) biphen-2-ylcarbonylamino]-3,4-dihydro-1H-isoquinolin-2-yl moiety.

The processes can be effected, generally:

(a) for a compound of formula I wherein X is carbonyl, by treating compound II with a carboxylic acid of formula Z—Y—COOH in the presence of a coupling reagent. The coupling reagent is typically a carbodiimide, preferably 1-ethyl-(3-dimethylaminopropyl)carbodiimide which is known by the acronym EDC and can be obtained commercially. The EDC can advantageously be polymer bound as disclosed in U.S. Pat. No. 5,416,193. The reaction is typically conducted at room temperature and in an inert solvent, although heating can be employed if desired. Typical reaction spans vary anywhere from a few minutes to 48 hours, typically overnight.

(b) for a compound of formula I wherein X is carbonyl or thiocarbonyl, by treating compound II with an activated form of a corresponding carboxylic acid or thiocarboxylic acid, in the presence of a base. Typically the activated form is the corresponding acid chloride of formula Z—Y—COCl or Z—Y—CSCl, respectively. The base is, for example, an amine which may advantageously be bound to a polymer to reduce cleanup, a typical bound base being polymer bound morpholinomethyl-polystyrene. The reaction is generally conducted at room temperature with stirring, shaking or other form of agitation for a time necessary to allow the reaction to proceed to a reasonable degree if not to completion, typically 2–48 hours, typically overnight.

Compounds made as disclosed in (a) and (b) above form structural types previously referred to as amides and thioamides.

(c) for a compound of formula I wherein X is carbonyl or thiocarbonyl and Y is NH, by treating compound II with, respectively, a corresponding isocyanate of formula Z—N=C=O orthioisocyanate of formula Z—N=C=S, respectively. The resulting products are compounds according to the invention referred to herein by structural type as ureas and thioureas, respectively. The reaction is generally conducted in an inert solvent, typically a halogenated hydrocarbon such as 1,2-dichloroethane, typically for a time of 2–48 hours, usually overnight.

(d) for a compound of formula I wherein X is sulfonyl, by treating compound II with a corresponding sulfonyl chloride of formula Z—Y—SO$_2$Cl. The resulting product is of the sulfonamide structural type. The reaction is typically conducted in an inert solvent such as a halogenated hydrocarbon (e.g., 1,2-dichloroethane), at room temperature for several hours or more, typically overnight.

(e) for a compound of formula I wherein X is CH$_2$ and Y is a direct link, by treating compound II with an aldehyde of formula Z—CHO in the presence of sodium triacetoxyborohydride. This is essentially the reductive amination reported in Abdel-Magid et al., Tetrahedron Lett., 31(39), 5595–5598 (1990). The resulting product is of the N-alkyl structural type. The reaction is conducted in an appropriate solvent such as a halogenated hydrocarbon, with shaking or agitating otherwise for a time of from a few hours to several days at room temperature, although heat can be applied to increase reaction rate if desired.

(f) for a compound of formula I wherein X is CH$_2$ and Y is a direct link, by treating a compound of the formula

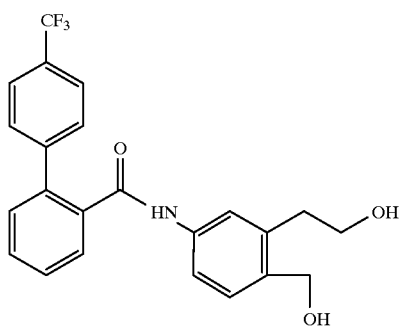

III with a corresponding compound of the formula Z—CH$_2$—NH$_2$, in the presence of mesyl chloride, typically two equivalents.

(g) for a compound of formula I wherein X is thiocarbonyl by treating a corresponding compound of formula I wherein X is CO with phosphorus pentasulfide, P$_4$S$_{10}$. The reaction can be carried out conventionally by using a stoichiometric amount of P$_4$S$_{10}$ (or an excess if desired) and heating it together with the corresponding amide in an inert solvent such as pyridine, xylene, benzene, chlorobenzene or toluene. The reaction is usually implemented at reflux for anywhere from a few minutes to a few hours.

The compound of formula II can be made as outlined in Scheme I and as specifically exemplified in Example 1. Referring to Scheme I, 2-(4-bromophenyl)ethylamine hydrobromide is reacted with ethyl formate in the presence of a base to make N-[2-(4-bromophenyl)ethyl]formamide. The fornamide is then treated with phosphorus pentoxide in polyphosphoric acid to cyclize, followed by treatment with hydrogen halide (e.g., HCl) gas to form the hydrohalide salt of 7-bromo-3,4-dihydroisoquinoline hydrohalide. The hydrohalide salt is then reduced to afford 7-bromo-1,2,3,4-tetrahydroisoquinoline. The reduced material is then nitrated by treatment with potassium nitrate in concentrated sulfuric acid and the appropriate fraction separated to yield 7-bromo6-nitro-1,2,3,4-tetrahydroisoquinoline. The nitrated material is then reacted with di-tert-butyl dicarbonate in the presence of a base to block the ring tetrahydroisoquinoline nitrogen, thereby affording 7-bromo-6-nitro-3,4-dihydro-1H-isoquinoline-2-carboxylic acid tert-butyl ester. The ester is then hydrogenated in the presence of palladium-on-calcium carbonate to form the corresponding 6-amino-3,4-dihydro-1H-isoquinoline-2-carboxylic acid ester. The amine is then reacted with 4'-trifluoromethylbiphenyl-2-carboxylic acid to form 6-[4'-trifluoromethylbiphenyl-2-carbonyl) amino]3,4-dihydro-1H-isoquinoline-2-carboxylic acid tert-butyl ester. This product can then be deblocked conventionally to make compound II, 4'-trifluoromethylbiphenyl-2-carboxylic acid (1,2,3,4tetrahydroisoquinolin-6-yl)amide.

SCHEME I

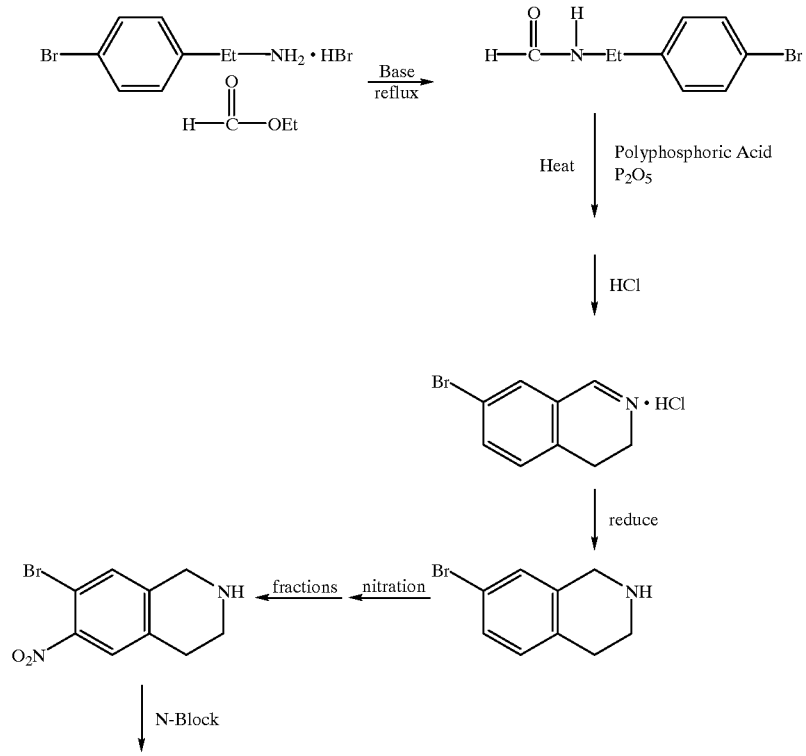

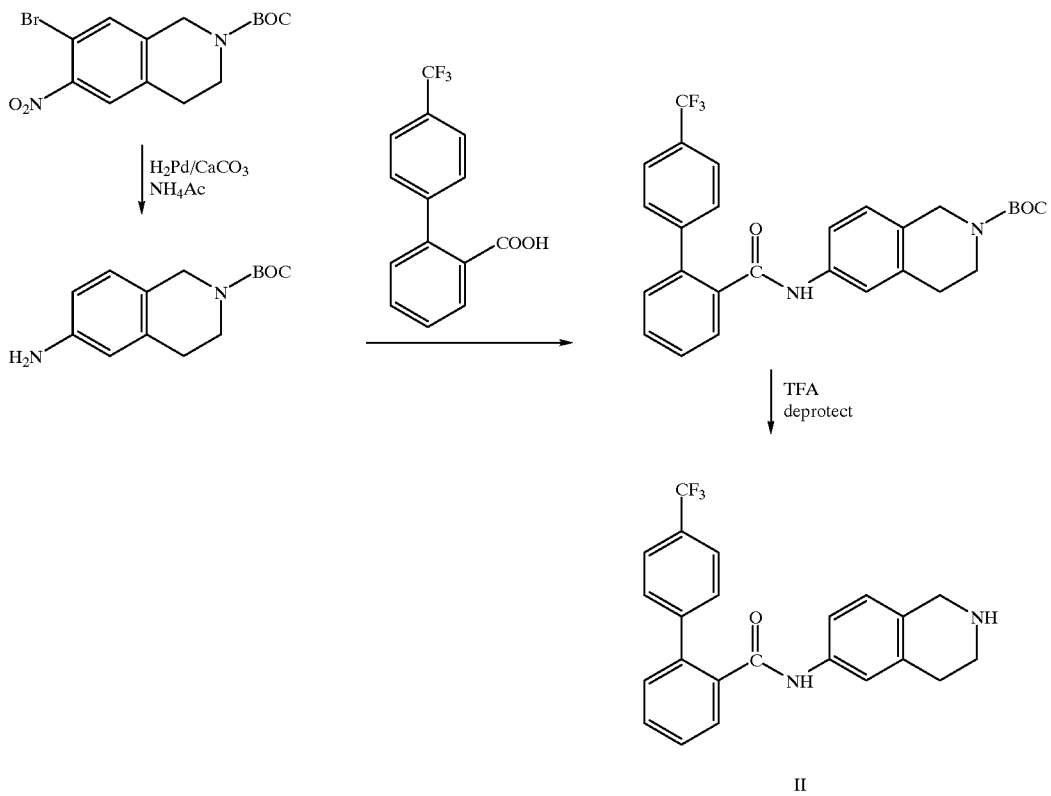

The compound of formula II can, alternatively, be made by a second route as illustrated in Scheme 2. Referring to Scheme 2, nitrobenzoic acid (1) can be treated with dimethyl malonate in the presence of base to form compound (2). Compound (2) can then be treated with aqueous alcoholic base to effect hydrolysis and decarboxylation to yield compound (3). Compound (3) can, if desired, be treated with acetic anhydride in toluene or other hydrocarbon solvent to make anhydride (3a). Reduction of compound (3) or (3a) affords the corresponding diol (4) which can then be treated with mesyl chloride to form the dimesylate which is subsequently cyclized with ammonia, thereby affording compound (5). Compound (5) is then conventionally N-blocked to yield compound (6), which in turn is reduced to make corresponding amine (7). Amine (7) can then be treated with the acid chloride of 4'-trifluoromethylbiphenyl-2-carboxylic acid (made by treating the corresponding free acid with thionyl chloride) to make the corresponding amide analog (8) of compound II. Compound (8) can be deblocked conventionally, as illustrated and discussed in Scheme I, to afford compound II.

SCHEME 2

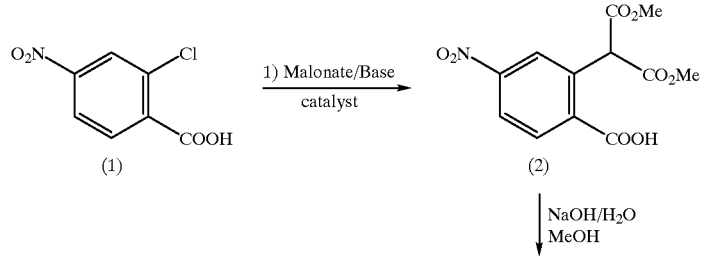

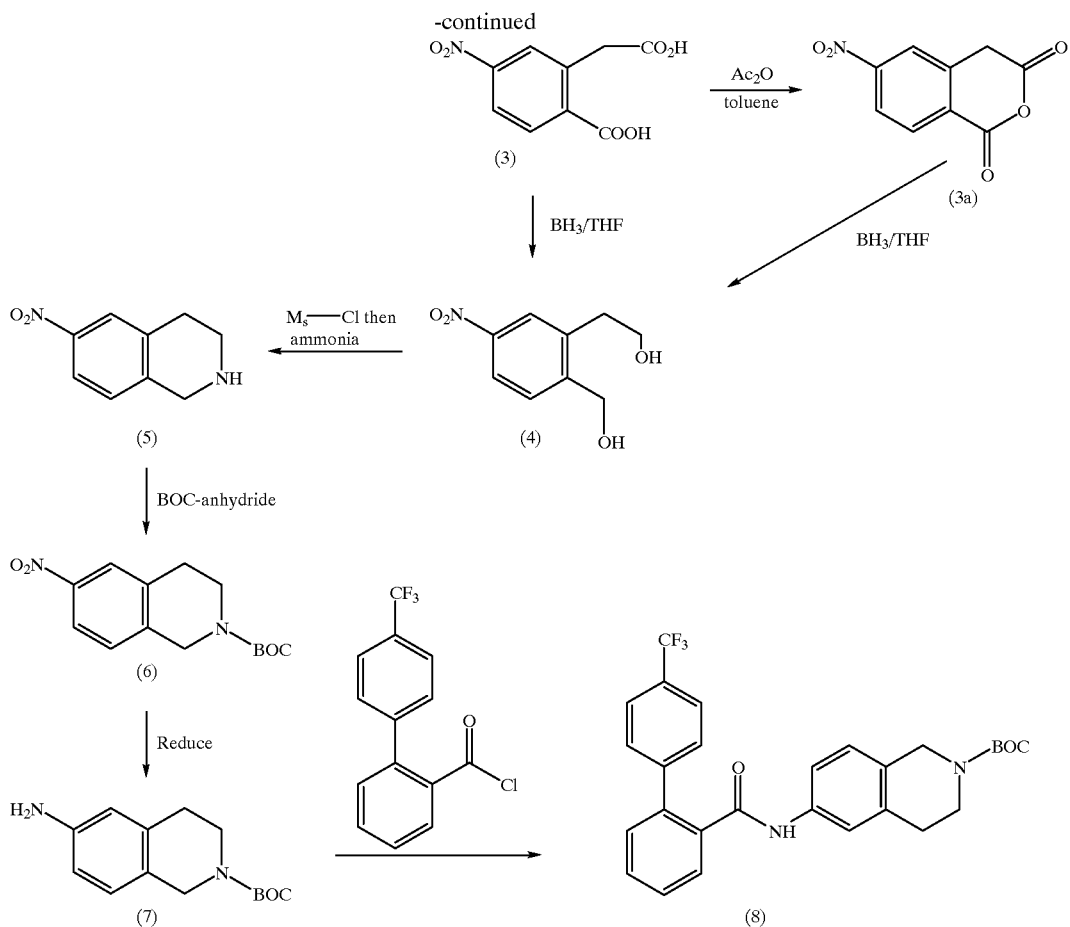

The compound of formula III can be made as illustrated in Scheme 3 starting with the diol (4) first shown in Scheme 2. Referring to Scheme (3), diol (4) is reduced with hydrogen in the presence of platinum-on-carbon catalyst to make corresponding amino diol (9). Amino diol (9) can then be reacted with the acid chloride of 4'-trifluoromethylbiphenyl-2-carboxylic acid to afford compound III. Compound III can, as shown, then be cyclized with ammonia in the presence of a catalyst to make compound II.

As also shown in Scheme 3, compound III can also be reacted directly with a corresponding amine of formula Z—CH$_2$—NH$_2$ in the presence of base and catalyst to make a compound of formula I, designated I$a$ in Scheme 3, wherein X is CH$_2$ and Y is a direct link.

SCHEME 3

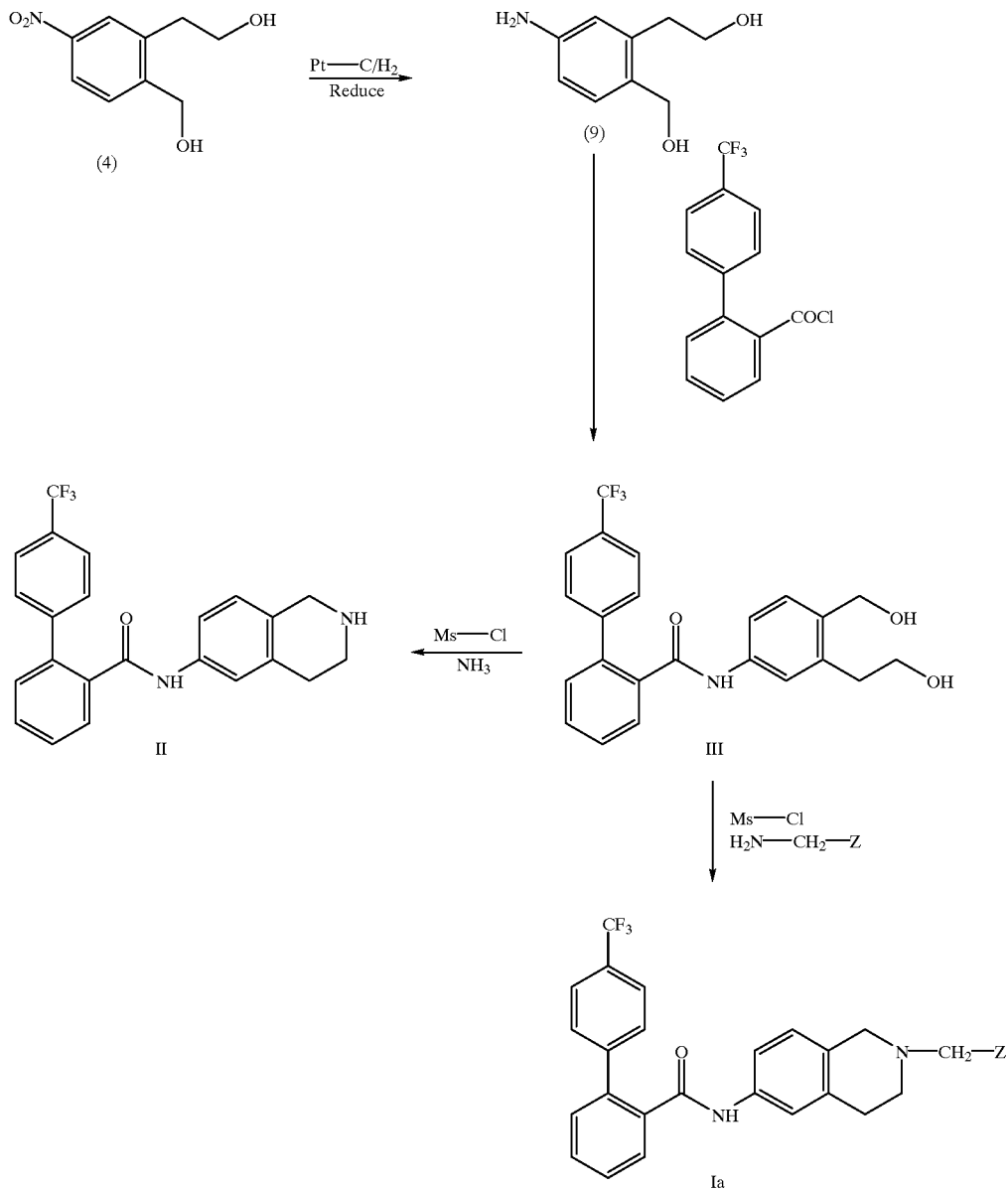

Conventional methods and/or techniques of purification and separation known to those skilled in the art can be used to isolate the compounds of this invention. Such techniques include all types of chromatography (HPLC, column chromatography using common adsorbents such as silica gel, and thin layer chromatography), recrystallization, and differential (i.e., liquid-iquid) extraction techniques.

The compounds herein form cationic salts such as acid addition salts and the expression "pharmaceutically-acceptable safts" is intended to define but not be limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts. For many compounds polyaddition salts are feasible.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The compounds of the present invention are orally administrable and are accordingly used in combination with a pharmaceutically acceptable carrier or diluent suitable to oral dosage forms. Suitable pharmaceutically-acceptable carriers include inert solid fillers or diluents and sterile aqueous or organic solutions. The active compound will be present in such pharmaceutical compositions in amounts sufficient to provide the desired dosage amount in the range described below. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. For parenteral administration the compounds can be combined with sterile aqueous or organic media to form injectable solutions or suspensions. Solutions or suspensions of these active compounds can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations contain a preservative to prevent the growth of microorganisms. The injectable solutions prepared in this manner can then be administered intravenously, intraperitoneally, subcutaneously, or intramuscularly.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syingability exists. It must be stable under the conditions of manufacture and storage and must be preserved against the contaminating action of microorganisms such as bacteria and fungi.

The dose of a compound of formula I which is administered will generally be varied according to principles well known in the art taking into account the severity of the condition being treated and the route of administration. In general, a compound of formula I will be administered to a warm blooded animal (such as a human) so that an effective dose, usually a daily dose administered in unitary or divided portions, is received, for example a dose in the range of about 0.1 to about 15 mg/kg body weight, preferably about 1 to about 5 mg/kg body weight. The total daily dose received will generally be between 1 and 1000 mg, preferably between 5 and 350 mg.

The compounds of this invention may be used in conjunction with other pharmaceutical agents, including other lipid lowering agents. Such agents include cholesterol biosynthesis inhibitors, especially HMG CoA reductase inhibitors and squalene synthetase inhibitors; bile acid sequestrants; fibrates; cholesterol absorption inhibitors; and niacin.

A test compound is considered to be active if it is active in any of the following screens.

The activity of a compound according to the invention can be assessed by measuring inhibition of apo B secretion in HepG2 cells.

HepG2 cells are grown in Dulbecco's Modified Eagles Medium plus 10% fetal bovine serum (growth medium; Gibco) in. 96well culture plates in a humidified atmosphere containing 5% carbon dioxide until they are approximately 70% confluent. Test compounds are dissolved at 10–20 mM in dimethyl sulfoxide which is then diluted to 1 $\mu$M in growth medium. Serial 1:1 dilutions of this stock are made in growth medium and 100 $\mu$l of each are added to separate wells of a 96-well culture plates containing HepG2 cells. Twenty four hours later, growth medium is collected and assayed by specific ELISA for apoB and, as a control, apoAl concentrations. Inhibitors are identified as compounds that decrease apoB secretion into the medium without affecting the secretion of apoAl. The ELISA for apoB is performed as follows. Monoclonal antibody against human apoB (Chemicon) is diluted to 5 $\mu$g/ml in phosphate buffered saline/azide (PBS+0.02% Na azide) and 100 $\mu$l are added to each well of a 96-well plate (NUNC Maxisorb). After an overnight incubation at room temperature, the antibody solution is removed and wells are washed 3 times with PBS/azide. Non-specific sites on the plastic are blocked by incubating wells for 1–3 hours in a solution of 1% (w/v) bovine serum albumin (BSA) made in PBS/azide. 100 $\mu$l of various dilutions of growth medium from the HepG2 cells or apoB standards (made in 0.04% Tween 20/1% BSA in PBS/azide) added to each well and incubated for 18 hours. Wells are aspirated and washed 3 times (0.1% Tween 20 in PBS) prior to adding 100 $\mu$l of a 1/1000 dilution of the secondary antibody, goat anti-human apoB (Chemicon). After a 3 hr incubation at room temperature, this solution is aspirated and the wells are again washed 3 times as above. 100 $\mu$l of a 1:1600 dilution (in PBS/1% BSA/2mM $MgCl_2$) of rabbit anti-goat IgG conjugated to alkaline phosphatase (Sigma) are then added to each well and incubated for 1 hr at room temperature. After aspirating, the wells are washed 4 times as above and 100 $\mu$l of 1 mg/ml p-nitrophenylphosphate (pNPP; Sigma) in 25 mM sodium (bi)carbonate/2 mM $MgCl_2$, pH 9.5, are added to each well and incubated for 20–30 minutes and then the reaction is terminated by the addition of 50 $\mu$l of 0.2N NaOH. Absorbance of each well is read at 405 nm and the background at 650 nm is subtracted. ApoB concentration is calculated from a standard curve constructed from purified LDL standards that are run in parallel in the same assay. ApoAl is measured in an analogous manner except that antibodies for apoAl (Chemicon) are used in place of the antibodies for apoB and antigen incubation is at 37° instead of room temperature.

Activity can also be confirmed if a test compound inhibits MTP activity directly.

Inhibition of MTP activity by a compound can be quantitated by observing the inhibition of transfer of radiolabeled triglyceride from donor vesicles to acceptor vesicles in the presence of soluble human MTP. The procedure for preparing MTP is based on the method of Wetterau and Zilversmit (Biochem. Biophys. Acta (1986) 875:610). Briefly, human liver chunks, frozen at −80° C., are thawed on ice, minced, and rinsed several times with ice cold 0.25M sucrose. All subsequent steps are performed on ice. A 50% homogenate in 0.25M sucrose is prepared using a Potter-Elvehjem Teflon pestle. The homogenate is diluted 1:1 with 0.25M sucrose and centrifuged at 10,000×g for 20 min at 4° C. The pellet is resuspended in sucrose and recentrifuged at 10,000×g for 20 min. The supernatants are combined and the microsomes pelleted by centrifugation at 105,000×g for 75 min. The supernatant is discarded and the microsomal pellet is suspended in a minimal volume of 0.25M sucrose, diluted to 3 ml per gm starting liver weight with 0.15M Tris-HCl pH 8.0. This suspension is divided into 12 fractions, and centrifuged at 105,000×g for 75 min. The supernatants are discarded and the microsomal pellets are stored frozen at −80° C. until needed. For preparation of MTP prior to performing the assay, a thawed pellet is suspended in 12 ml of cold 50 mM Tris-HCl, 50 mM KCl, 5 mM MgCl, pH 7.4 and 1.2 ml of a 0.54% deoxycholate (pH 7.4) solution is added slowly with mixing to disrupt the microsomal membrane. After a 30 min incubation on ice with gentle mixing, the suspension is centrifuged at 105,000×g for 75 min. The supernatant, containing the soluble MTP protein, is dialyzed for 2–3 days with 4 changes of assay buffer (150 mM Tris-HCl, 40 mM NaCl, mM EDTA, 0.02% NaN3, pH 7.4). The human liver MTP is stored at 4° C. and diluted 1:5 with assay buffer just before use. MTP preparations show no notable loss of transfer activity with storage up to 30 days.

Liposomes are prepared under nitrogen by room temperature, bath sonication of a dispersion of 400$\mu$M egg phosphatidylcholine (PC), 75$\mu$M bovine heart cardiolipin, and 0.82 $\mu$M [14C]-triolein (110 Cl/mol) in assay buffer. The lipids in chloroform are added in the proper amounts and dried under a nitrogen stream before hydrating with assay buffer. Acceptor liposomes are prepared under nitrogen by room temperature bath sonication of a dispersion of 1.2 mM PC, 2.3 $\mu$M triolein and 30 pM [3H]-PC (50 Ci/mol) in assay buffer. The donor and acceptor liposomes are centrifuged at 160,000×g for 2 hrs at 7° C. The top 80% of the supernatant, containing small unilamellar liposomes, are carefully removed and stored at 4° C. until used for transfer assays.

MTP activity is measured using a transfer assay which is initiated by mixing donor and acceptor vesicles together with the soluble MTP and test compound. To 100 $\mu$l of either a 5% BSA (control) or 5% BSA containing the test compound, are added 500 $\mu$l assay buffer, 100 $\mu$l donor liposomes, 200 $\mu$l acceptor liposomes and 100 $\mu$l of diluted MTP protein. After incubation at 37° C. for 45 min., triglyceride transfer is terminated by adding 500 $\mu$l of a 50% (w/v) DEAE cellulose suspension in assay buffer. Following 4 min of agitation, the donor liposomes, bound to the DEAE cellulose, are selectively sedimented by low speed centrifugation. An aliquot of the supernatant containing the acceptor liposomes is counted and the 3H and 14C counts are used to calculate the percent recovery of acceptor liposomes and the percent triglyceride transfer using first order kinetics. Inhibition of triglyceride transfer by test compound is manifest as a decrease in 14C radioactivity compared to controls where no test compound is present.

Actity of test compounds as MTP inhibitors can also be measured in vivo according to the following test.

Male mice (20–39 g.; various strains) are dosed by oral gavage (0.25-ml/25 g. body weight) with test compound suspended in an aqueous 0.5% methyl cellulose solution. Compound solutions are dosed either multiple times over several days or, alternatively, once 90 minutes before mice are euthanized and blood is collected for preparation of serum. The serum is assayed for triglyceride concentration by a commercial enzymatic assay (Triglyceride G: Wako Fine Chemicals). MTP inhibitors are identified by their ability to lower serum triglycerides as compared to control mice dosed with vehicle.

The present invention is illustrated by the following Examples. However, it should be understood that the invention is not limited to the specific details of these examples.

EXAMPLE 1

This example illustrates how to make the intermediate compound of formula II N-[2-(4-Bromo-phenyl)-ethyl]-formamide 500 g (1.78 mol) of 2-(4-bromo-phenyl)-ethylamine hydrobromide, 1 liter (12.4 mol) of ethyl formate and 248 ml (1.78 mol) of triethylamine were combined and heated to reflux for 3 hrs. The reaction was treated with 1 liter each of deionized water and ethyl acetate. The organic layer was separated and washed with 1 liter each of water and brine. The organic layer was dried over anhydrous magnesium sulfate, filtered and concentrated to yield 378 g of a solid.

MS (Cl): 245(M+NH$_4^+$)
7-Bromo-3,4-dihydro-isoquinoline hydrochloride

In a 12 liter three neck round bottom flask, 4 kg of polyphosphoric acid was heated to 150° C. and stirred. To the stirring polyphosphoric acid was added 530 g (3.75 mol) of phosphorus pentoxide in three portions of approximately 176.7 g each. After the phosphorus pentoxide had dissolved, 378 g (1.66 mol) of N-[2-(4bromo-phenyl)-ethyl]-formamide was added. The reaction temperature was then raised to 200° C. and maitained for two hours. At this point, the reaction temperature was allowed to cool to 160° C. and poured onto 16 liters of ice. The mixture was stirred for 0.5 hours, basified to pH 12 with 10N sodium hydroxide solution and extracted three times with 3 liters of dichloromethane. The combined organic layers were washed with 1 liter of saturated sodium chloride solution, dried over anhydrous sodium sulfate, filtered and concentrated to an oil. The oil was dissolved in 2.5 liters of methanol and saturated with anhydrous HCl gas. The resulting solution was concentrated to one liter volume and 1 liter of diethyl ether was added. The resulting precipitate was filtered, washed with diethyl ether and air dried to yield 219 g of a solid.

MS (Cl): 210 (M+H$^+$)
7-Bromo-1,2,3,4-tetrahydroisoquinoline 219 g (0.89 mol) of 7-bromo-3,4-dihydro-isoquinoline hydrochloride and 1.5 liters of water were combined and heated to 50° C. 33.7 g (0.89 mol) of sodium borohydrde was added in portions over 0.5 hours at which time the temperature rose to 62° C. The reaction was then cooled to ambient temperature and extracted three times with 1 liter of dichloromethane. The combined organic layers were washed with 1 liter of saturated sodium chloride solution, dried over anhydrous sodium sulfate and concentrated to yield 173 g of an oil.

MS (Cl): 212 (M+H$^+$)
7-Bromo-6-nitro-1,2,3,4-tetrahydroisoquinoline

In a 5 liter three neck round bottom flask, 173 9 (0.813 mol) of 7-bromo-1,2,3,4-tetrahydroisoquinoline was dissolved carefully into 950 ml of concentrated sulfuric acid. The resulting solution was cooled to −5° C. and a solution of 82.7 g (0.816 mol) of potassium nitrate in 1 liter of concentrated sulfuric acid was added dropwise. After addition, the reaction was maintained at −5° C. for 15 minutes and poured onto 3 liters of ice. The resulting mixture was basified to pH 14 with 50% sodium hydroxide solution. The basic solution was extracted three times with 1 liter of dichloromethane. The combined organic layers were washed with 1 liter each of water and saturated sodium chloride solution. The organic layer was dried over anhydrous sodium sulfate, filtered and concentrated to yield 201 g of an oil. The oil preadsorbed onto silica gel was charged onto a column of 4 kg of silica gel and eluted with a gradient of 1–5% methanol/dichloromethane. The fractions containing product were combined and concentrated to yield 115 g of a solid.

$^1$H NMR (300 MHz, CDCl$_3$) δ 7.61 (s, 1H); 7.38 (s, 1H); 4.10 (s, 2H); 3.20 (t, 2H); 2.90 (t, 2H).

7-Bromo-6-nitro-3,4-dihydro-1H-isoquinoline-2-carboxlic acid tert-butyl ester 115 g (0.447 mol) of 7-bromo-6-nitro-1,2,3,4-tetrahydroisoquinoline, 45.2 g (0.447 mol) of TEA, 97.5 g (0.447 mol) of di-tert-butyl dicarbonate, 3.2 liter of dioxane and 0.5 liter of water were combined and stirred at ambient temperature for 1.5 hrs. The reaction was concentrated to remove the dioxane, 1 liter of saturated sodium bicarbonate was added and extracted two times with 1 liter of dichloromethane. The organic layer was extracted with brine, dried over magnesium sulfate and concentrated. The resulting solid was recrystallized from isopropanol to yield 118 g of a solid.

$^1$H NMR (250 MHz, DMSO) δ 7.89 (s, 1H); 7.81 (s, 1H); 4.58 (s, 2H); 3.56 (t, 2H); 2.81 (t, 2H); 1.42 (s, 9H).

6Amino-3,4-dihydro-1H-isoquinoline-2-carboxylic acid tert-butyl ester 59 g (0.16 mol) of 7-bromo-6-nitro-3,4-dihydro-1H-isoquinolin-2-carboxylic acid tert-butyl ester, 10 g of 5% palladium on calcium carbonate and 49 g of ammonium acetate in 1 liter of acetic acid was hydrogenated on a Parr shaker for 5 hrs. The reaction was filtered through CELITE®concentrated, basified to pH 12 with 4N sodium hydroxide and extracted with methylene chloride. The organic layer was washed with water, brine, dried over magnesium sulfate and concentrated to yield 40 g of an oil.

$^1$H NMR (300 MHz, DMSO) δ 4.87 (s, 2H); 4.27 (s, 2H); 3.44 (t, 2H); 2.57 (t, 2H); 1.39 (s, 9H).

6-[(4'-Trifluoromethyl-biphenyl-2-carbonyl)-amino]-3,4-dihydro-1H-isoquinoline-2-carboxylic acid tert-butyl ester 7.6 g (29 mmol) of 4'-trifluoromethyl-biphenyl-2-carboxylic acid, 7.1 g (29 mmol) of 6-amino-3,4-dihydro-1H-isoquinoline-2-caboxyiic acid tert-butyl ester, 100 mg of DMAP and 6.1 g (32 mmol) of EDCl were mixed in 130 ml of methylene chloride for 12 hrs. Reaction was extracted with 2×150 ml 1N HCl, 2×150 ml 1N NaOH, 150 ml water, brine and concentrated to yield 14 g of a beige foam.

MS (Cl): 519 (M+Na$^+$)

$^1$H NMR (250 MHz, CDCl$_3$) δ 4.49 (s, 2H); 3.60 (t, 2H); 2.77 (t, 2H).

4'-Trifluoromethyl-biphenyl-2-carboxylic acid (1,2,3,4tetrahydroisoquinolin-6-yl)-amide 4 g (8 mmol) of 6-[(4'-trifiuoromethyl-biphenyl-2-carbonyl)-amino]-3,4-dihydro-1H-isoquinoline-2-carboxylic acid tert-butyl ester and 6 ml (78 mmol) of TFA were mixed in 60 ml of methylene chloride for 5 hrs. 40 ml of methylene chloride was added and organic was extracted with 3×50 ml of saturated sodium bicarbonate and brine. Organic layer was dried over sodium sulfate and concentrated to yield 3.1 gm of solid.

MS (Cl): 397 (M+H$^+$)

The following compounds, classified as amides by the criteria previously set forth, were synthesized by the procedure described in method A.

Method A

Into a glass screw topped vial was placed 150 μl of a 0.020M solution of the acid chloride in 1,2-dichloroethane (3.0 μmol), followed by 83 μl of 0.030M 4'-trifluoromethyl-biphenyl-2-carboxylic acid (1,2,3,4-tetrahydroisoquinolin-6-yl)-amide in 1,2-dichloroethane (2.5 μmol), followed by 25 mg polymer bound morpholinomethylpolystyrene (@2.5 μmol/gm=62 μmol). After shaking at 20° C. for 16 hours, 10 μl was removed and diluted to 100 μl with methanol for RPHPLC and MS analysis. The polymer was removed by filtration and the filtrate was concentrated to dryness under vacuum.

EXAMPLE 2

By Method A described above, 4'-trifluoromethyl-biphenyl-2-carboxylic acid [2-(3-cyclopentyl-propionyl)-1,2,3,4-tetrahydroisoquinolin-6-yl]-amide was made by reacting compound II with 3-cyclopentylpropionyl chloride in the presence of polymer-bound morpholine.

MS (Cl): 521 (M+H$^+$)

EXAMPLES 3–39

The following compounds were made according to methods analogous to those described in Example 2 by reacting compound II with the approprate corresponding acid chloride.

4'-Trifluoromethyl-biphenyl-2-carboxylic acid (2-phenylacetyl-1,2,3,4-tetrahydrosoquinolin-6-yl)-amide MS (Cl): 515 (M+H$^+$); $^1$H NMR (250 MHz, CDCl$_3$) δ 4.68 and 4.53 (s, 2H); 3.80 (s, 2H); 3.80 and 3.61 (t, 2H); 2.76 and 2.59 (t, 2H).

4'-Trifluoromethyl-biphenyl-2-carboxylic acid (2-benzoyl-1,2,3,4-tetrahydroisoquinolin-6-yl)-amide MS (Cl): 501 (M+H$^+$)

4'-Trifluoromethyl-biphenyl-2-carboxylic acid [2-(furan-2-carbonyl)-1,2,3,4tetrahydrosoquinolin-6-yl]-amide MS (Cl): 491 (M+H$^+$)

4'-Trifluoromethyl-biphenyl-2-carboxylic acid [2-(4-chloro-butyryl)-1,2,3,4-tetrahydroisoquinolin-6-yl]-amide MS (Cl): 501 (M+H$^+$)

4'-Trifluoromethyl-biphenyl-2-carboxylic acid (2-benzyloxyacetyl-1,2,3,4-tetrahydroisoquinolin-6-yl)-amide MS (Cl): 545 (M+H$^+$)

4'-Trifluoromethyl-biphenyl-2-carboxylic acid [2-(4-heptyl-benzoyl)-1,2,3,4-tetrahydroisoquinolin-6-yl]-amide MS (Cl): 599 (M+H$^+$)

4'-Trifluoromethyl-biphenyl-2carboxylic acid [2-(bicyclo[2.2.1]hept-5-ene-2-carbonyl)-1,2,3,4-tetrahydroisoquinolin-6-yl]-amide MS (Cl): 517 (M+H$^+$)

4'-Trifluoromethylbiphenyl-2-carboxylic acid [2-(5-methyl-5-phenyl-isoxazole-4-carbonyl)-1,2,3,4-tetrahydroisoquinolin-6-yl]-amide MS (Cl): 582 (M+H$^+$)

4'-Trifluoromethyl-biphenyl-2-carboxylicacid(2-tetradecanoyl-1,2,3,4-tetrahydroisoquinolin-6-yl)-amide MS (Cl): 607 (M+H$^+$)

4'-Trifluoromethyl-biphenyl-2-carboxylic acid [2-(3,3-dimethyl-butyryl)-1,2,3,4-tetraydroisoquinolin-6-yl]-amide MS (Cl): 495 (M+H$^+$)

4'-Trifluoromethyl-biphenyl-2-carboxylic acid (2-phenoxyacetyl-1,2,3,4-tetrahydroisoquinolin-6-yl)-amide MS (Cl): 531 (M+H+)

Aceticacid2oxo-1-phenyl-2-{6-[(4'-trifluoromethyl-biphenyl-2-carbonyl)-amino]-3,4-dihydro-1H-isoquinolin-2-yl}-ethyl ester MS (Cl): 573 (M+H+)

4'-Trifluoromethyl-biphenyl-2carboxylic acid [2-(thiophene-2-carbonyl)-1,2,3,4-tetrahydroisoquinolin-6-yl]-amide MS (Cl): 507 (M+H+)

4'-Trifluoromethyl-biphenyl-2-carboxylic acid [2-(2,2,5,7-tetramethyl-1-oxo-indane-4carbonyl)-1,2,3,4-tetrahydroisoquinolin-6-yl]-amide MS (Cl): 611 (M+H+)

4'-Trifluoromethyl-biphenyl-2-carboxylic acid (2-octanoyl-1,2,3,4-tetrahydro-isoquinolin-6-yl)-amide MS (Cl): 523 (M+H+)

4'-Trifluoromethyl-biphenyl-2-carboxylic acid (2-octadec-9-enoyl-1,2,3,4-tetrahydroisoquinolin-6-yl)-amide MS (Cl): 661 (M+H+)

4'-Trifluoromethyl-biphenyl-2-carboxylicacid [2-(quinoxaline-2-carbonyl)-1,2,3,4-tetrahydroisoquinolin-6-yl]-amide MS (Cl): 553 (M+H+)

4-Oxo-4-{6-[(4'-trifluoromethyl-biphenyl-2-carbonyl)-amino]-3,4-dihydro-1H-isoquinolin-2-yl}-butyric acid methyl ester MS (Cl): 511 (M+H+)

4'-Trifluoromethyl-biphenyl-2-carboxylic acid [2-(biphenylcarbonyl)-1,2,3,4-tetrahydroisoquinolin-6-yl]-amide MS (Cl): 577 (M+H+)

4'-Trifluoromethyl-biphenyl-2-carboxylic acid (2pentanoyl-1,2,3,4tetrahydro-isoquinolin-6-yl)-amide MS (Cl): 481 (M+H+)

4'-Trifluormethy-biphenyl-2-carboxylic acid (2-isobutyryl-1,2,3,4tetrahydroisoquinolin-6-yl)-amide MS (Cl): 467 (M+H+)

4'-Trifluoromethyl-biphenyl-2-carboxylic acid (2-decanoyl-1,2,3,4-tetrahydroisoquinolin-6-yl)-amide MS (Cl): 551 (M+H+)

4'-Trifluoromethyl-biphenyl-2-carboxylic acid (2-octadecanoyl-1,2,3,4-tetrahydroisoquinolin-6-yl)-amide MS (Cl): 663 (M+H+)

4'-Trifluoromethyl-biphenyl-2-carboxylic acid (2-hexanoyl-1,2,3,4-tetrahydroisoquinolin-6-yl)amide MS (Cl): 495 (M+H+)

4'-Trifluoromethyl-biphenyl-2-carboxylic acid [2-(3-phenyl-propionyl)-1,2,3,4-tetrahydroisoquinolin-6-yl]-amide MS (Cl): 529 (M+H+)

4'-Trifluoromethyl-biphenyl-2-carboxylic acid (2-cyclohexanecarbonyl-1,2,3,4-tetrahydroisoquinoin-6-yl)-amide MS (Cl): 507 (M+H+)

4'-Trifluoromethyl-biphenyl-2-carboxylic acid (2-cyclobutanecarbonyl-1,2,3,4-tetrahydroisoquinolin-6-yl)-amide MS (Cl): 479 (M+H+)

4'-Trifluoromethyl-biphenyl-2-carboxylic acid [2-(2-ethyl-hexanoyl)-1,2,3,4-tetrahydroisoquinolin-6-yl]-amide MS (Cl): 523 (M+H+)

3-Oxo-3-{6-[(4'-trifluoromethyl-biphenyl-2-carbonyl)-amino]-3,4-dihydro-1H-isoquinolin-2-yl}-propionic acid methyl ester MS (Cl): 497 (M+H+)

5-Oxo-5-{6-[(4'-trifluoromethyl-biphenyl-2-carbonyl)-amino]-3,4-dihydro-1H-isoquinolin-2-yl}-pentanoic acid methyl ester MS (Cl): 525 (M+H+)

4'-Trifluoromethyl-biphenyl-2-carboxylic acid [2-(2-chloro-propionyl)-1,2,3,4-tetrahydroisoquinolin-6-yl]-amide MS (Cl): 487 (M+H+)

5-Oxo-5-{6-[(4'-trifluoromethyl-biphenyl-2-carbonyl)-amino]-3,4-dihydro-1H-isoquinolin-2-yl}-pentanoic acid ethyl ester MS (Cl): 539 (M+H+)

4'-Trifluoromethyl-biphenyl-2-carboxylic acid {2-[(3-methoxyphenyl)-acetyl]-1,2,3,4tetmhydroisoquinolin-6-yl}-amide MS (Cl): 545 (M+H+)

4'-Trifluoromethyl-biphenyl-2-carboxylic acid [2-(thiophen-2-yl-acetyl)-1,2,3,4-tetrahydroisoquinolin-6-yl]-amide MS (Cl): 521 (M+H+)

$^1$H NMR (250 MHz, CDCl$_3$) δ 4.68 and 4.60 (s, 2H); 3.97(s, 2H); 3.80 and 3.69 (t, 2H); 2.71 (m, 2H).

4'-Trifluoromethyl-biphenyl-2-carboxylic acid (2-butyryl-1,2,3,4-tetrahydro-isoquinolin-6-yl)-amide MS (Cl): 467 (M+H+)

4-Oxo-4-{6-[(4'-trifluoromethyl-biphenyl-2-carbonyl)-amino]-3,4dihydro-1H-isoquinolin-2-yl}-butyric acid methyl ester MS (Cl): 511 (M+H+)

4'-Trifluoromethyl-biphenyl-2-carboxylic acid (2octadec-11-enoyl-1,2,3,4-tetrahydroisoquinolin-6-yl)-amide MS (Cl): 661 (M+H+)

METHOD B

Polymer bound EDC 1-(3-dimethylaminopropyl)-3-ethylcarbodiimide hydrochloride (20 gm, 0.104 mol) was partitioned between 400 ml methylene chloride, 200 ml water, and 100 ml concentrated ammonium hydroxide. The aqueous layer was extracted with 2×100 ml methylene chloride. The combined organic layers were washed with 100 ml 10% ammonium hydroxide solution, 100 ml water, dried over magnesium sulfate, filtered and concentrated under vacuum to a clear colorless oil. The oil was dissolved in 350 ml DMF, Merrifield resin (100 gm. 2% dvb, 200–400 mesh, 1.0 mmol/gm) was added and the stirred mbdure was heated at 100° C. for 16 hours. After cooling, the resin was filtered, washed with 2×200 ml DMF, 2 times 300 ml THF, and dried in a 50° C. vacuum oven for 20 hours. IR 2131 cm$^{-1}$.

Reaction

Into a glass screw topped vial was placed 50 μl of a 0.050M solution of the acid in 1,2-dichloroethane (2.5 umol), followed by 50 μl of 0.050M compound II in 1,2-dichloroethane (2.5 μmol), followed by 30 μl 0.017M DMAP in 1,2-dichloroethane (0.5 μmol), followed by 25 mg polymer bound 1-(3-dimethylaminopropyl)-3ethylcarbodiimide (@1.0 μmol/gm=25 μmol). After shaking at 20° C. for 16 hours, 1 μl was removed and diluted to 100 μl with methanol for RPHPLC and MS analysis. The polymer was removed by filtration and the filtrate was concentrated to dryness under vacuum.

EXAMPLE 40

4'-Trifluoromethyl-biphenyl-2-carboxylic acid [2-(naphthalen-2-yl-acetyl)-1,2,3,4-tetrahydroisoquinolin-6-yl]-amide was made by reacting compound II with naphthalene-2-ylacetic acid in the presence of polymer bound EDC as described in METHOD B above.

MS (Cl): 565 (M+H$^+$)

EXAMPLES 41–97

The following compounds were made by reacting compound II with the appropriate corresponding carboxylic acid in the presence of polymer bound EDC, according to methods analogous to that described in Example 40.

4'-Trifluoromethyl-biphenyl-2-carboxylic acid [2-(2,2-dimethyl-propionyl)-1,2,3,4-tetrahydroisoquinolin-6-yl]-amide MS (Cl): 481 (M+H$^+$)

4'-Trifluoromethyl-biphenyl-2-carboxylicacid [2-(2,2-dimethyl-pentanoyl)-1,2,3,4-tetrahydroisoquinolin-6-yl]-amide MS (Cl): 509 (M+H$^+$)

4'-Trifluoromethyl-biphenyl-2-carboxylic acid [2-(3-hydroxy-2-phenyl-propionyl)-1,2,3,4-tetrahydroisoquinolin-6-yl]-amide MS (Cl): 545 (M+H$^+$)

4'-Trifluoromethylbiphenyl-2-carboxylic acid [2-(2-phenyl-butyryl)-1,2,3,4-tetrahydroisoquinolin-6-yl]-amide MS (Cl): 543 (M+H$^+$)

4'-Trifluoromethyl-biphenyl-2-carboxylic acid [2-(3-methyl-4-oxo-pentanoyl)-1,2,3,4-tetrahydroisoquinolin-6-yl]-amide MS (Cl): 509 (M+H$^+$)

4'-Trifluoromethyl-biphenyl-2-carboxylic acid [2-(2-ethyl-butyryl)-1,2,3,4-tetrahydroisoquinolin-6-yl]-amide MS (Cl): 495 (M+H$^+$)

4'-Trifluoromethyl-biphenyl-2-boxylic acid (2-ethoxyacetyl-1,2,3,4-tetrahydroisoquinolin-6-yl)-amide MS (Cl): 483 (M+H$^+$)

4'-Trifluoromethyl-biphenyl-2-oarboxylic acid {2-[(4-fluoro-phenyl)-acetyl]-1,2,3,4-tetrahydroisoquinolin-6-yl}-amide MS (Cl): 533 (M+H$^+$)

4'-Trifluoromethyl-biphenyl-2-carboxylic acid (2-phenylthioacetyl-1,2,3,4-tetrahydroisoquinolin-6-yl)-amide MS (Cl): 547 (M+H$^+$)

4'-Trifluoromethyl-biphenyl-2-carboxylic acid (2-benzylthioacetyl-1,2,3,4-tetrahydroisoquinolin-6-yl)-amide MS (Cl): 561 (M+H$^+$)

4'-Trifluoromethyl-biphenyl-2-carboxylic acid [2-(3-methyl-butyryl)-1,2,3,4-tetrahydroisoquinolin-6-yl]-amide MS (Cl): 481 (M+H$^+$)

4'-Trifluoromethyl-biphenyl-2-carboxylic acid [2-(3-chloro-butyryl)-1,2,3,4-tetrahydroisoquinolin-6-yl]-amide MS (Cl): 501 (M+H$^+$)

4'-Trifluoromethyl-biphenyl-2-carboxylic acid (2-but-3-enoyl-1,2,3,4-tetrahydroisoquinolin-6-yl)-amide MS (Cl): 465 (M+H$^+$)

4'-Trifluoromethyl-biphenyl-2-carboxylic acid [2-(1-cetyl-pyrrolidine-2-carbonyl)-1,2,3,4-tetrahydroisoquinolin-6-yl]-amide MS (Cl): 536 (M+H$^+$)

4'-Trifluoromethyl-biphenyl-2-carboxylic acid {$^2$-[(4-oxo-2-thioxo-thiazolidin-3-yl)-acetyl]-1,2,3,4-tetrahydroisoquinolin-6-yl}-amide MS (Cl): 570 (M+H$^+$)

4'-Trifluoromethyl-biphenyl-2-carboxylic acid [2-(pyridine-4-carbonyl)-1,2,3,4-tetrahydroisoquinolin-6-yl]-amide MS (Cl): 502 (M+H$^+$)

4'-Trifluoromethyl-biphenyl-2-rboxylic acid [2-(quinoline-2-carbonyl)-1,2,3,4-tetrahydroisoquinolin-6-yl]-amide MS (Cl): 552 (M+H$^+$)

4'-Trifluoromethyl-biphenyl-2-carboxylic acid [2-(1-phenyl-cyclopentane-carbonyl)-1,2,3,4-tetrahydroisoquinolin-6-yl]-amide MS (Cl): 569 (M+H$^+$)

4'-Trifluoromethybiphenyl-2-carboxylic acid [2-(a-methoxy-pheny-acetyl)-1,2,3,4-tetrahydroisoquinolin-6-yl]-amide MS (Cl): 545 (M+H$^+$)

4'-Trifluoromethyl-biphenyl-2-carboxylic aid [2-(3-chloro2,2-dimethylpropionyl)-1,2,3,4-tetrahydroisoquinolin-6-yl]amide MS (Cl): 515 (M+H$^+$)

4'-Trifluoromethyl-biphenyl-2-carboxylic acid (2-cyanoacetyl-1,2,3,4-tetrahydroisoquinolin-6-yl)-amide MS (Cl): 464 (M+H$^+$)

4'-Trifluoromethyl-biphenyl-2-carboxylic acid (2-methoxyacetyl-1,2,3,4-tetrahydroisoquinolin-6-yl)-amide MS (Cl): 469 (M+H$^+$)

4'-Trifluoromethyl-biphenyl-2-coxylic acid {2-[(4-chloro-phenyl)-acetyl]-1,2,3,4-tetrahydroisoquinolin-6-yl}-amide MS (Cl): 549 (M+H$^+$)

4'-Trifluoromethyl-biphenyl-2-carbcxylic acid (2-ethyfthioacetyl-1,2,3,4-tetrahydroisoquinolin-6-yl)-amide MS (Cl): 499 (M+H$^+$)

4'-Trifluoromethyl-biphenyl-2-caboxyic acid [2-(3-phenyl-prop-2-ynoyl)-1,2,3,4-tetrahydroisoquinolin-6-yl]-amide MS (Cl): 525 (M+H$^+$)

4-Trifluoromethyl-biphenyl-2-coxylic acid [2-(3hydroxy-butyryl)-1,2,3,4-tetrahydroisoquinolin-6-yl]-amide MS (Cl): 483 (M+H$^+$)

4'-Trifluoromethyl-biphenyl-2-carboxylic acid {2-[(1H-indol-3-yl)acetyl]-1,2,3,4-tetrahydroisoquinolin-6-yl}-amide MS (Cl): 554 (M+H$^+$)

4-Trifluoromethyl-biphenyl-2-carboxylic acid [2-(6-methyl-pyridine-2-carbonyl)-1,2,3,4-tetrahydroisoquinolin-6-yl]amide MS (Cl): 516 (M+H$^+$)

4'-Trifluoromethyl-biphenyl-2-carboxylic acid [2-(pyridin-2-yl-acetyl)-1,2,3,4-tetrahydroisoquinolin-6-yl]-amide MS (Cl): 516 (M+H$^+$)

$^1$H NMR (300 MHz, CDCl$_3$) δ 4.67 (s, 2H); 3.99 (s, 2H); 3.77 (m, 2H); 2.76 and 2.65 (t, 2H).

4'-Trifluoromethyl-biphenyl-2-carboxylic acid {2-[(4-nitro-phenyl)-acetyl]-1,2,3,4-tetrahydroisoquinolin-6-yl}-amide MS (Cl): 560 (M+H$^+$)

4'-Trifluoromethyl-biphenyl-2-carboxylic acid [2-(6-diethylcarbamoyl-cyclohex-3-enecarbonyl)-1,2,3,4-tetrahydroisoquinolin-6-yl]-amide MS (Cl): 604 (M+H$^+$)

4'-Trifluoromethyl-biphenyl-2-carboxylic acid [2-(adamantane-1-carbonyl)-1,2,3,4-tetrahydroisoquinolin-6-yl]-amide MS (Cl): 559 (M+H$^+$)

4'-Trifluoromethyl-biphenyl-2-carboxylic acid {2-[(3-chloro-phenyl)-acetyl]-1,2,3,4-tetrahydroisoquinolin-6-yl}-amide MS (Cl): 549 (M+H+)

4'-Trifluoromethyl-biphenyl-2-carboxylic acid (2-diphenylacetyl-1,2,3,4-tetrahydroisoquinolin-6-yl)-amide MS (Cl): 591 (M+H$^+$)

4'-Trifluoromethyl-biphenyl-2-carboxylic acid {2-[(2,4-dichloro-phenyl)-acetyl]-1,2,3,4-tetrahydroisoquinolin-6-yl}-amide MS (Cl): 583 (M+H$^+$)

4'-Trifluoromethyl-biphenyl-2-carboxylic acid [2-(2-phthalimido-acetyl)-1,2,3,4-tetrahydroisoquinolin-6-yl]-amide MS (Cl): 584 (M+H$^+$)

4'-Trifluoromethyl-biphenyl-2-carboxylic acid [2-(biphenyl-4-yl-acetyl)-1,2,3,4-tetrahydroisoquinolin-6-yl]-amide MS (Cl): 591 (M+H$^+$)

4'-Trifluoromethyl-biphenyl-2-carboxylic acid (2-o-tolylacetyl-1,2,3,4-tetrahydroisoquinolin-6-yl)-amide MS (Cl): 529 (M+H$^+$)

4'-Trifluoromethyl-biphenyl-2-carboxylic acid (2-m-tolylacetyl-1,2,3,4-tetrahydroisoquinolin-6-yl)-amide MS (Cl): 529 (M+H$^+$)

4'-Trifluoromethyl-biphenyl-2-carboxylic acid [2-(4-phenyl-but-3-enoyl)-1,2,3,4-tetrahydroisoquinolin-6-yl]-amide MS (Cl): 541 (M+H$^+$)

4'-Trifluoromethyl-biphenyl-2-carboxylic acid [2-(cyclopent-1-enylacetyl)-1,2,3,4-tetrahydroisoquinolin-6-yl]-amide MS (Cl): 505 (M+H$^+$)

4'-Trifluoroethyl-biphenyl-2-carboxylic acid {2-[(3,4,5-methoxy-phenyl)-acetyl]-1,2,3,4-tetrahydroisoquinolin-6-yl}-amide MS (Cl): 605 (M+H$^+$)

4'-Trifluoromethyl-biphenyl-2-carboxylic acid [2-(adamant-1-yl-acetyl)-1,2,3,4-tetrahydroisoquinolin-6-yl]-amide MS (Cl): 573 (M+H$^+$)

4'-Trifluoromethyl-biphenyl-2-carboxylic acid [2-(9H-fluorene9-carbonyl)-1,2,3,4-tetrahydroisoquinolin-6-yl]-amide MS (Cl): 589 (M+H$^+$)

4'-Trifluoromethyl-biphenyl-2-carboxylic acid {2-[(3-trifluoromethyl-phenyl)-acetyl]-1,2,3,4-tetrahydroisoquinolin-6-yl}-amide MS (Cl): 583 (M+H$^+$)

4'-Trifluoromethyl-biphenyl-2-carboxylic acid [2-(1-methyl-cyclohexane-carbonyl)-1,2,3,4-tetrahydroisoquinolin-6-yl]-amide MS (Cl): 521 (M+H$^+$)

4'-Trifluoromethyl-biphenyl-2-carboxylic acid {2-[2-(1,3-dioxo-1,3dihydro-isoindol-2-yl)-propionyl]-1,2,3,4-tetrahydroisoquinolin-6-yl}-amide MS (Cl): 598 (M+H$^+$)

4'-Trifluoromethyl-biphenyl-2-carboxylic acid [2-(4-methyl-2-oxo-pentanoyl)-1,2,3,4-tetrahydroisoquinolin-6-yl]-amide MS (Cl): 509 (M+H$^+$)

4'-Trifluoromethyl-biphenyl-2-carboxylic acid [2-(3-methoxy-cyclohexanecarbonyl)-1,2,3,4-tetrahydroisoquinolin-6-yl]-amide MS (Cl): 537 (M+H$^+$)

4'-Trifluoromethyl-biphenyl-2-carboxylic acid (2-hex-3-enoyl-1,2,3,4-tetrahydroisoquinolin-6-yl)-amide MS (Cl): 493 (M+H$^+$)

2-{6-[(4'-Trifluoromethyl-biphenyl-2-carbonyl)-amino]-3,4-di hydro-1H-isoquinoline-2-carbonyl}-pyrrolidine-1-carboxylic acid tert-butyl ester

MS (CI): 594 (M+H$^+$)

4'-Trifluoromethyl-biphenyl-2-carboxylic acid [2-(tetrahydro-furan-3-carbonyl)-1,2,3,4-tetrahydroisoquinolin-6-yl]-amide MS (Cl): 495 (M+H$^+$)

4'-Trifluoromethyl-biphenyl-2-carboxylic acid [2-(a-oxo-thiophen-2-yl-acetyl)-1,2,3,4-tetrahydroisoquinolin-6-yl]-amide MS (Cl): 552 (M+NH$_4^+$)

4'-Trifluoromethyl-biphenyl-2-carboxylic acid [2-(thiophen-3-yl-acetyl)-1,2,3,4-tetrahydroisoquinolin-6-yl]-amide MS (Cl): 521 (M+H$^+$)

4'-Trifluoromethyl-biphenyl-2-carboxylic acid {2-[(6-methoxy-3-oxo-indan-1-yl)-acetyl]-1,2,3,4-tetrahydroisoquinolin-6-yl}-amide MS (Cl): 600 (M+2)

4'-Trifluoromethyl-biphenyl-2-carboxylic acid [2-(1-acetyl-pyrrolidine-2-carbonyl)-1,2,3,4-tetrahydroisoquinolin-6-yl]-amide MS (Cl): 536 (M+H$^+$)

4'-Trifluoromethyl-biphenyl-2-carboxylic acid [2-(bicyclo[2.2.1]hept-2-yl-acetyl)-1,2,3,4-tetrahydroisoquinolin-6-yl]-amide MS (Cl): 533 (M+H$^+$)

EXAMPLE 98

Compound II (200 mg, 0.50 mmol), picolinic acid (62 mg, 0.60 mmol) and EDCl (116 mg, 0.60 mmol) were mixed in 10 ml methylene chloride for 14 hrs. Reaction was concentrated and purified by flash chromatography on silica gel (eluent: 70–100% EtOAc/Hex). The product was 4'-Trifluoromethyl-biphenyl-2-carboxylic acid [2-(pyridine-2-carbonyl)-1,2,3,4-tetrahydroisoquinolin-6-yl]-amide, 98% yield.

MS (Cl): 502 (M+H$^+$);

$^1$H NMR (250 MHz, CDCl) δ 4.81 and 4.69 (s, 2H); 3.92 and 3.73 (t, 2H); 2.83 (m, 2H).

METHOD C

Into a glass screw topped vial was placed 150 μl of a 0.020M solution of the isocyanate in 1,2-dichloroethane (3.0 μmol), followed by 83 μl of 0.030M 4'-trifluoromethyl-biphenyl-2-carboxylic acid (1,2,3,4-tetrahydroisoquinolin-6-yl)-amide (compound II) in 1,2-dichloroethane (2.5 μmol) After shaking at 20° C. for 16 hours, 10 μl was removed and diluted to 100 μl with methanol for RPHPLC and MS analysis. The reaction was concentrated to dryness under vacuum.

EXAMPLE 99

6-[(4'-Trifluoromethyl-biphenyl-2-carbonyl)-amino]-3,4-dihydro1H-isoquinoline-2-carboxylic acid phenylamide was made as described in Method C by reacting compound II with phenyl isocyanate.

MS (Cl): 516 (M+H$^+$);

$^1$H NMR (250 MHz, DMSO) δ 4.56 (s, 2H); 3.66 (t, 2H); 2.77 (t, 2H).

EXAMPLES 100–103

The following compounds were made by reacting compound II with the appropriate corresponding isocyanate according to methods analogous to those described in Example 99.

6-[4'-Trifluoromethylbiphenyl-2-carbonyl)-amino]-3,4-dihydro-1H-1soquinoline-2-carboxylic acid hexylamide MS (Cl): 524 (M+H$^+$)

({6-[(4'-Trifluoromethyl-biphenyl-2-carbonyl)-amino]-3,4-dihydro-1H-isoquinoline-2-carbonyl}-amino)-acetic acid ethyl ester MS (Cl): 526 (M+H$^+$)

6-[(4'-Trifluoromethyl-biphenyl-2-carbonyl)-amino]-3,4-dihydro-1H-isoquinoline-2-carboxylic acid benzylamide MS (Cl): 530 (M+H$^+$)

6[(4'-Trifluoromethyl-biphenyl-2carbonyl)-amino]-3,4-dihydro-1H-isoquinoline-2-carboxylic acid [(R)-1-phenyl-ethyl]-amide Note: Product made as described in Method C using compound II and (R)-(+)-α-methylbenzyl isocyanate.

MS (Cl): 544 (M+H$^+$);

$^1$H NMR (250 MHz, CDCl$_3$) δ 5.06 (m, 1H); 4.66 (d, 1H); 4.46 (s, 2H); 3.56 (t,2H); 2.78 (t, 2H); 1.52 (d, 3H).

EXAMPLE 104

6-[(4'-Trifluoromethyl-biphenyl-2-carbonyl)-amino]-3,4-dihydro-1H-isoquinoline-2-carboxylic acid pyridin-2-ylamide was prepared by a method analogous to the procedure described in Ohsawa, A.; Arai, H.; Igeta, H. *Chem. Pharm. Bull.* 1980, 28, 3570.

23% yield;

MS (Cl): 517 (M+H$^+$);

$^1$H NMR (300 MHz, CDCl$_3$) δ 4.60 (s, 2H); 3.69 (t, 2H); 2.86 (t, 2H).

METHOD D

Into a glass screw topped vial was placed 150 μl of a 0.020M solution of the sulfonyl chloride in 1,2-dichloroethane (3.0 μmol), followed by 83 μl of 0.030M compound II in 1,2-dichloroethane (2.5μmol), followed by 25 mg polymer bound morpholinomethylpolystyrene(@2.5 mmol/gm=62 μmol). After shaking at 20° C. for 16 hours, 10 μl was removed and diluted to 100 μl with methanol for RPHPLC and MS analysis. The polymer was removed by filtration and the filtrate was concentrated to dryness under vacuum.

EXAMPLE 105

4'-Trifluoromethyl-biphenyl-2-carboxylic acid [2-(naphthalene-1-sulfonyl)-1,2,3,4-tetrahydroisoquinolin6-yl]-amide was prepared by METHOD D reacting compound II with naphthalene-1-sulfonyl chloride.

MS (Cl): 604 (M+NH$_4^+$)

EXAMPLES 106–111

The following compounds were prepared by METHOD D as in Example 105, by reacting compound II with the appropriate correspondin sulfonyl chloride.

2-{6-[(4'-Trifluoromethyl-biphenyl-2-carbonyl)-amino]-3,4dihydro-1H-isoquinoline-2-sulfonyl}-benzoic acid methyl ester MS (Cl): 595 (M+H$^+$)

4'-Trifluoromethyl-biphenyl-2-carboxylic acid [2-(propane-2-sulfonyl)-1,2,3,4-tetrahydroisoquinolin-6-yl]-amide MS (Cl): 520 (M+NH$_4^+$)

4'-Trifluoromethyl-biphenyl-2-carboxylic acid [2-(3-chloro-propane-1-sulfonyl)-1,2,3,4tetrahydroisoquinolin-6-yl]-amide MS (Cl): 555 (M+NH$_4^+$)

4'-Trifluoromethyl-biphenyl-2-carboxylic acid [2-(butane-1-sulfonyl)-1,2,3,4-tetrahydroisoquinolin-6-yl]-amide MS (Cl): 534 (M+NH$_4^+$)

4'-Trifluoromethyl-biphenyl-2-carboxylic acid (2-dimethylsulfamoyl-1,2,3,4-tetrahydroisoquinolin-6-yl)-amide MS (Cl): 521 (M+NH$_4^+$)

4'-Trifluoromethyl-biphenyl-2-carboxylic acid [2-(2-trifluoromethoxy-benzenesulfonyl)-1,2,3,4-tetrahydroisoquinolin-6-yl]-amide MS (Cl): 638 (M+NH$_4^+$)

EXAMPLE 112

This example illustrates how to make a compound where the group in XYZ linking XYZ to the tetrahydroisoquinoline ring is thiocarbamoyl.

Into a glass screw topped vial was placed 150 μl of a 0.020M solution of the thioisocyanate (cyclopropyihioisocyanate) in 1,2-dichloroethane (3.0 umol), followed by 83 μl of 0.030M 4'-trifluoromethyl-biphenyl-2 carboxylic acid (1,2,3,4-tetrahydroisoquinolin6-yl)-amide in 1,2-dichloroethane (2.5 μmol) After shaking at 20° C. for 16 hours, 10 μl was removed and diluted to 100 μl with methanol for RPHPLC and MS analysis. The reaction was concentrated to dryness under vacuum, yielding 4'-trifluoromethyl-biphenyl-2-carboxylic acid (2-cyclopropylthiocarbamoyl-1,2,3,4tetrahydroisoquinolin-6-yl)-amide MS (Cl): 496 (M+H$^+$)

METHOD F

A solution of aldehyde (7.5 μmol), compound II (5μmol), acetic acid (7.5 μmol), and sodium triacetoxyborohydride (10 μmol) in 300 μl of 1,2-dichloroethane was shaken for 60 hr at room temperature. A 7.5 μl sample was removed and diluted with 93 μl of methanol for TLC and MS analysis. The remaining sample was evaporated to dryness in vacuo. The crude solid was dissolved in 500 μl of ethyl acetate and washed with 300 µl of 5% sodium bicarbonate. The organic layer was concentrated to dryness under vacuum.

EXAMPLE 113

4'-Trifluoromethyl-biphenyl-2-carboxylic acid [2-(2,6,6trimethyl-cyclohexyl-2-enylmethyl)-1,2,3,4-tetrahydroisoquinolin-6yl]-amide was made as described in METHOD F by reacting compound II with 2,6,6-trimethylcyclohex-2-enyl aldehyde.

MS (Cl): 533 (M+H$^+$)

EXAMPLES 114–162

The following compounds were made as in Example 113 by METHOD F by reacting compound II with the appropriate corresponding aldehyde.

4'-Trifluoromethyl-biphenyl-2-carboxylic acid (2-cyclohex3-enylmethyl-1,2,3,4-tetrahydroisoquinolin-6-yl)-amide MS (Cl): 491 (M+H$^+$)

4'-Trifluoromethyl-biphenyl-2-carboxylic acid [2-(3-methyl-benzyl)-1,2,3,4-tetrahydroisoquinolin-6-yl]-amide MS (Cl): 501 (M+H$^+$)

4'-Trifluoromethyl-biphenyl-2-carboxylic acid [2-(4-dimethylamino-benzyl)-1,2,3,4tetrahydroisoquinolin-6-yl]-amide MS (Cl): 530 (M+H$^+$)

4'-Trifluoromethyl-biphenyl-2-carboxylic acid [2-(4methoxy-benzyl)-1,2,3,4-tetrahydroisoquinolin-6-yl]-amide MS (Cl): 517 (M+H$^+$)

4'-Trifluoromethyl-biphenyl-2-carboxylic acid [2-(2-fluoro-benzyl)-1,2,3,4-tetrahydroisoquinolin-6-yl]-amide MS (Cl): 505 (M+H$^+$)

4'-Trifluoromethyl-biphenyl-2-carboxylic acid [2-(3,4-dichloro-benzyl)-1,2,3,4-tetrahydroisoquinolin-6-yl]-amide MS (Cl): 555 (M+H$^+$)

4'-Trifluoromethyl-biphenyl-2-carboxylic acid [2-(4-isopropyl-benzyl)-1,2,3,4-tetrahydroisoquinolin-6-yl]-amide MS (Cl): 529 (M+H$^+$)

4'-Trifluoromethyl-biphenyl-2-carboxylic acid (2-biphenyl-4-ylmethyl-1,2,3,4-tetrahydroisoquinolin-6-yl)-amide MS (Cl): 564 (M+2)

4'-Trifluoromethyl-biphenyl-2-carboxylic acid [2-(3-phenoxy-benzyl)-1,2,3,4-tetrahydroisoquinolin-6-yl]-amide MS (Cl): 580 (M+2)

4'-Trifluoromethyl-biphenyl-2-carboxylic acid [2-(4methoxy-naphthalen-1-ylmethyl)-1,2,3,4-tetrahydroisoquinolin-6-yl]-amide MS (Cl): 568 (M+2)

4'-Trifluoromethyl-biphenyl-2-carboxylic acid (2-naphthalen-1-ylmethyl-1,2,3,4-tetrahydroisoquinolin-6-yl)-amide MS (Cl): 538 (M+2)

4'-Trifluoromethyl-biphenyl-2-carboxylic acid [2-(4-methylthio-benzyl)-1,2,3,4-tetrahydroisoquinolin-6-yl]-amide MS (Cl): 533 (M+H$^+$)

4'-Trifluoromethyl-biphenyl-2-carboxylic acid [2-(9-ethyl-9H-carbazol-3-ylmethyl)-1,2,3,4-tetrahydroisoquinolin-6-yl]-amide MS (Cl): 605 (M+2)

4'-Trifluoromethyl-biphenyl-2-carboxylic acid [2-(4-tert-butyl-benzyl)-1,2,3,4-tetrahydroisoquinolin-6-yl]-amide MS (Cl): 544 (M+2)

3-{6-[(4'-Trifluoromethyl-biphenyl-2-carbonyl)-amino]-3,4-dihydro-1H-isoquinolin-2-ylmethyl}-cyclohexanecarboxylic acid ethyl ester MS (Cl): 566 (M+2)

4'-Trifluoromethyl-biphenyl-2-carboxylic acid [2-(2-tert-butylthio-benzyl)-1,2,3,4-tetrahydroisoquinolin6-yl]-amide MS (Cl): 576 (M+2)

4'-Trifluoromethyl-biphenyl-2-carboxylic acid (2-cyclohexylmethyl-1,2,3,4-tetrahydroisoquinolin-6-yl)-amide MS (Cl): 494 (M+2)

4'-Trifluoromethyl-biphenyl-2-carboxylic acid [2-(3-fluoro-benzyl)-1,2,3,4-tetrahydroisoquinolin-6yl]-amide MS (Cl): 505 (M+H$^+$)

4'-Trifluoromethyl-biphenyl-2-carboxylic acid (2-benzo[1,3]dioxol-5-ylmethyl-1,2,3,4-tetrahydroisoquinolin-6-yl)-amide MS (Cl): 531 (M+H$^+$)

4'-Trifluoromethyl-biphenyl-2-carboxylic acid (2-naphthalen-2-ylmethyl-1,2,3,4-tetrahydroisoquinolin-6yl)-amide MS (Cl): 538 (M+2)

4'-Trifluoromethyl-biphenyl-2-carboxylic acid [2-(2-methoxy-naphthalen-1-ylmethyl)-1,2,3,4-tetrahydroisoquinolin-6-yl]-amide MS (Cl): 568 (M+2)

4'-Trifluoromethyl-biphenyl-2-carboxylic acid [2-(4benzyloxy3methoxy-benzyl)-1,2,3,4-tetrahydroisoquinolin-6yl]-amide MS (Cl): 624 (M+2)

4'-Trifluoromethyl-biphenyl-2-carboxylic acid [2-(1,3,4-trimethyl-cyclohexyl-3-enylmethyl)-1,2,3,4-tetrahydroisoquinolin-6-yl]-amide MS (Cl): 533 (M+H$^+$)

4'-Trifluoromethyl-biphenyl-2-carboxylic acid {2-[2-(4-chloro-phenylthio)-benzyl]-1,2,3,4-tetrahydroisoquinolin-6-yl}-amide MS (Cl): 629 (M+H$^+$)

4'-Trifluoromethyl-biphenyl-2-carboxylic acid [2-(2,4dichloro-benzyl)-1,2,3,4-tetrahydroisoquinolin-6-yl]-amide MS (Cl): 555 (M+H$^+$)

4'-Trifluoromethyl-biphenyl-2-carboxylic acid [2-(1,5a,6,9,9a,9b-hexahydro-4H-dibenzofuran-4a-ylmethyl)-1,2,3,4-tetrahydroisoquinolin-6-yl]-amide MS (Cl): 585 (M+H$^+$)

4'-Trifluoromethyl-biphenyl-2-carboxylic acid {2-[4(2-diethylamino-ethoxy)-benzyl]-1,2,3,4-tetrahydroisoquinolin-6-yl}-amide MS (Cl): 603 (M+2)

4'-Trifluoromethyl-biphenyl-2-carboxylic acid [2-(2-trifluoromethyl-benzyl)-1,2,3,4-tetrahydroisoquinolin-6-yl]-amide MS (Cl): 555 (M+H$^+$)

4'-Trifluoromethyl-biphenyl-2-carboxylic acid [2-(6,6-dimethyl-bicyclo[3.1.1]hept-2-en-2-ylmethyl)-1,2,3,4-tetrahydroisoquinolin-6-yl]-amide

MS (CI): 531 (M+H⁺)

4'-Trifluoromethyl-biphenyl-2-carboxylic acid [2-(2-benzyloxy-benzyl)-1,2,3,4-tetrahydroisoquinolin-6-yl]-amide

MS (CI): 594 (M+2)

4'-Trifluoromethyl-biphenyl-2-carboxylic acid [2-(4-phenoxy-benzyl)-1,2,3,4- tetrahydroisoquinolin-6-yl]-amide

MS (CI): 579 (M+H⁺)

4'-Trifluoromethyl-biphenyl-2-carboxylic acid [2-(4-dimethylamino-naphthalen-1-ylmethyl)-1,2,3,4-tetrahydroisoquinolin-6-yl]-amide

MS (CI): 580 (M+H⁺)

4'-Trifluoromethyl-biphenyl-2-carboxylic acid [2-(4-pyrrolidine-1-yl-benzyl)-1,2,3,4-tetrahydroisoquinolin-6-yl]-amide

MS (CI): 557 (M+2)

4'-Trifluoromethyl-biphenyl-2-carboxylic acid (2-thiophen-2-ylmethyl-1,2,3,4-tetrahydroisoquinolin-6-yl)-amide

MS (CI): 493 (M+H⁺);

¹H NMR (250 MHz, DMSO) δ 3.83 (s, 2H); 3.52 (s, 2H); 2.69 (m, 4H).

4'-Trifluoromethyl-biphenyl-2-carboxylic acid [2-(1H-indol-3-ylmethyl)-1,2,3,4-tetrahydroisoquinolin-6-yl]-amide

MS (CI): 526 (M+H⁺)

4'-Trifluoromethyl-biphenyl-2-carboxylic acid [2-(1H-pyrrol-2-ylmethyl)-1,2,3,4-tetrahydroisoquinolin-6-yl]-amide

MS (CI): 476 (M+H⁺);

¹H NMR (300 MHz, DMSO) δ 3.54 (s, 2H); 3.43 (s, 2H); 2.72 (m, 2H); 2.60 (m, 2H).

4'-Trifluoromethyl-biphenyl-2-carboxylic acid (2-furan-2-ylmethyl-1,2,3,4-tetrahydroisoquinolin-6-yl)-amide

MS (CI): 477 (M+H⁺);

¹H NMR (250 MHz, DMSO) 3.65 (s, 2H); 3.47 (s, 2H); 2.71 (m, 2H); 2.65 (m, 2H).

4'-Trifluoromethyl-biphenyl-2-carboxylic acid [2-(1,5-dimethyl-3-oxo-2-phenyl-2,3-dihydro-1H-pyrazol-4-ylm ethyl)-1,2,3,4-tetrahydroisoquinolin-6-yl]-amide

MS (CI): 598 (M+2)

4'-Trifluoromethyl-biphenyl-2-carboxylic acid [2-(2,5-dimethyl-1-phenyl-1H-pyrrol-3-ylmethyl)-1,2,3, 4tetrahydroisoquinolin-6-yl]-amide

MS (CI): 581 (M+2)

4'-Trifluoromethyl-biphenyl-2-carboxylic acid [2-(3,5-dimethyl-1phenyl-1H-pyrazol-4-ylmethyl)-1,2,3,4-tetrahydroisoquinolin-6-yl]-amide

MS (CI): 582 (M+2)

4'-Trifluoromethyl-biphenyl-2-carboxylic acid (2-benzofuran-2-ylmethyl-1,2,3,4-tetrahydroisoquinolin-6yl)-amide

MS (CI): 527 (M+H⁺)

Aceticacid5-{6-[(4'-trifluoromethyl-biphenyl-2-carbonyl)-amino]-3,4-dihydro-1H-isoquinolin-2-ylmethyl}-furan-2-ylmethyl ester

MS (CI): 549 (M+H⁺);

¹H NMR (300 MHz, CDCl₃) δ 5.02 (s, 2H); 3.70 (s, 2H); 3.60 (s, 2H); 2.83 (t, 2H); 2.75 (t, 2H); 2.07 (s, 3H).

4'-Trifluoromethyl-biphenyl-2-carboxylic acid [2-(3-methyl-thiophen-2-ylmethyl)-1,2,3,4-tetrahydroisoquinolin-6-yl]-amide

MS (CI): 507 (M+H⁺)

4'-Trifluoromethyl-biphenyl-2-carboxylic acid (2-thiophen3-ylmethyl-1,2,3,4-tetrahydroisoquinolin-6-yl)-amide

MS (CI): 493 (M+H⁺)

4'-Trifluoromethyl-biphenyl-2-carboxylic acid [2-(2-methyl-1H-indol-3-ylmethyl)-1,2,3,4-tetrahydroisoquinolin-6-yl]-amide

MS (CI): 540 (M+H⁺)

2-Methyl-{6-[(4'-trifluoromethyl-biphenyl-2-carbonyl)-amino]-3,4-dihydro-1H-isoquinolin-2-ylmethyl}-furan-3-carboxylic acid ethyl ester

MS (CI): 563 (M+H⁺)

4'-Trifluoromethyl-biphenyl-2-carboxylic acid [2-(2,5methyl-thiophen-3-ylmethyl)-1,2,3,4-tetrahydroisoquinolin-6-yl]-amide

MS (CI): 541 (M+H⁺)

4'-Trifluoromethyl-biphenyl-2-carboxylic acid [2-(1methyl-1H-indol-3-ylmethyl)-1,2,3,4-tetrahydroisoquinolin-6-yl]-amide

MS (CI): 557 (M+NH₄⁺)

2-{6-[(4'-Trifluoromethyl-biphenyl-2-carbonyl)-amino]-3,4-di hydro-1H-isoquinolin-2-ylmethyl}-cyclopropanecarboxylic acid ethyl ester

MS (CI): 523 (M+H⁺)

METHOD G

The following compounds were made via reductive amination by methods analogous to the procedure described in Abdel-Magid, A. F.; Maryanoff, C. A.; Carson, K. G. *Tetrahedron Lett.* 1990, 31, 5595. This procedure is essentially the same as METHOD F and employs sodium triacetoxyborohydride, except that certain modifications, generally in the choice of solvent and reaction temperature have been made, all modifications being noted for each compound. In addition, unless otherwise noted, 1.5–2 equivalents of carbonyl compound was used. For compounds made in this section, it is noted that the free base was isolated. For use in biological screens the free base was, in most cases, converted to the mono-hydrochloride salt by conventional methods.

EXAMPLE 163

4'-Trifluoromethyl-biphenyl-2carboxylic acid (2-benzyl-1,2,3,4-tetrahydroisoquinolin-6-yl)-amide was made by reacting compound II with benzaldehyde, using a method analogous to that described in Abdel-Magid et al. above, with the following modifications:
Solvent: DCE
56% yield
MS (CI): 487 (M+H⁺)
¹H NMR (250 MHz, DMSO) δ 3.62 (s, 2H); 3.46 (s, 2H); 2.74 (m, 2H); 2.63 (m, 2H).

EXAMPLES 164–193

The following compounds were made by reacting compound II with the appropriate corresponding aldehyde using methods analogous to that disclosed in Abdel-Magid et al., with appropriate modifications noted.

4'-Trifluoromethyl-biphenyl-2-carboxylic acid (2-pyridin-2-ylmethyl-1,2,3,4-tetrahydroisoquinolin-6-yl)-amide Solvent THF
62% yield
MS (Cl): 488 (M+H⁺)
¹H NMR (300 MHz, CDCl₃) δ 3.82 (s, 2H); 3.63 (s, 2H); 2.84 (m, 2H); 2.77 (m, 2H).

4'-Trifluoromethyl-biphenyl-2-carboxylic acid (2-pyridin-3-ylmethyl-1,2,3,4-tetrahydroisoquinolin-6-yl)-amide
Solvent: THF
MS (Cl): 488 (M+H⁺)

4'-Trifluoromethyl-biphenyl-2carboxylic acid (2-pyridin-4-ylmethyl-1,2,3,4-tetrahydroisoquinolin-6-yl)-amide
Solvent: THF
MS (Cl): 488 (M+H⁺)

4'-Trifluoromethyl-biphenyl-2-carboxylic acid (2-quinolin-2-ylmethyl-1,2,3,4-tetrahydroisoquinolin-6-yl)-amide
Solvent: DCE
66% yield
MS (Cl): 538 (M+H⁺)
¹H NMR (250 MHz, CDCl₃) δ 3.99 (s, 2H); 3.67 (s, 2H); 2.82 (s, 4H).

4'-Trifluoromethyl-biphenyl-2-carboxylic acid [2-(6methyl-pyridin-2-ylmethyl)-1,2,3,4tetrahydroisoquinolin-6-yl]-amide
Solvent: DCE
63% yield
MS (Cl): 502 (M+H⁺)
¹H NMR (250 MHz, CDCl₃) δ 3.79 (s, 2H); 3.63 (s, 2H); 2.81 (s, 2H); 2.76 (s, 2H); 2.55 (s, 3H).

4'-Trifluoromethyl-biphenyl-2-carboxylic acid [2-(6-bromo-pyridin-2-ylmethyl)-1,2,3,4-tetrahydroisoquinolin-6-yl]-amide
Solvent: DCE
MS (Cl): 568 (M+H⁺)

4'-Trifluoromethyl-biphenyl-2-carboxylic acid [2-(6-formyl-pyridin-2-ylmethyl)-1,2,3,4-tetrahydroisoquinolin-6-yl]-amide
Solvent: DCE; 10 equiv. of aldehyde used
MS (Cl): 516 (M+H⁺)

4'-Trifluoromethyl-biphenyl-2-carboxylic acid [2-(2-chloro-benzyl)-1,2,3,4-tetrahydroisoquinolin-6-yl]-amide
Solvent: DCE
MS (Cl): 521 (M+H⁺)

4'-Trifluoromethyl-biphenyl-2-carboxylic acid [2-(3-chloro-benzyl)-1,2,3,4-tetrahydroisoquinolin-6-yl]-amide
Solvent: DCE
69% yield
MS (Cl): 521 (M+H⁺)
¹H NMR (300 MHz, DMSO) δ 3.64 (s, 2H); 3.47 (s, 2H); 2.74 (t, 2H); 2.64 (t, 2H).

4'-Trifluoromethyl-biphenyl-2-carboxylic acid [2-(4-chloro-benzyl)-1,2,3,4-tetrahydroisoquinolin-6-yl]-amide
Solvent: DCE
MS (Cl): 521 (M+H⁺)

4'-Trifluoromethyl-biphenyl-2-carboxylic acid (2-pyrimidin-2-ylmethyl-1,2,3,4-tetrahydroisoquinolin-6-yl)-amide
Solvent: Methylene chloride; 6 equiv. of aldehyde used
61% yield
MS (Cl): 489 (M+H⁺)
¹H NMR (250 MHz, DMSO) δ 3.87 (s, 2H); 3.60 (s, 2H); 2.77 (m, 4H).

4'-Trifluoromethyl-bipheny-2-carboxylic acid [2-(3-nitro-benzyl)-1,2,3,4-tetrahydroisoquinolin-6-yl]-amide
Solvent: DCE
76% yield
MS (Cl): 532 (M+H⁺)
¹H NMR (300 MHz, CDCl₃) δ 3.75 (s, 2H); 3.58 (s, 2H); 2.84 (t, 2H); 2.73 (t, 2H).

4'-Trifluoromethyl-biphenyl-2-carboxylic acid [2-(3-methoxy-benzyl)-1,2,3,4-tetrahydroisoquinolin-6-yl]-amide
Solvent: DCE
MS (Cl): 517 (M+H⁺)

4'-Trifluoromethyl-biphenyl-2-carboxylic acid [2-(3-trifuoromethyl-benzyl)-1,2,3,4tetrahydroisoquinolin-6-yl]-amide
Solvent: DCE
MS (Cl): 555 (M+H⁺)

4'-Trifluoromethyl-biphenyl-2-carboxylic acid [2-(3-cyano-benzyl)-1,2,3,4-tetrahydroisoquinolin6-yl]-amide
Solvent: DCE
MS (Cl): 512 (M+H⁺)

4'-Trifluoromethyl-biphenyl-2-carboxylic acid [2-(3-hydroxy-benzyl)-1,2,3,4-tetrahydroisoquinolin-6-yl]-amide
Solvent: DCE
MS (Cl): 503 (M+H⁺)

4'-Trifluoromethyl-biphenyl-2-carboxylic acid [2-(3,5-dichloro-benzyl)-1,2,3,4-tetrahydroisoquinolin-6-yl]-amide
Solvent: DCE
MS (Cl): 556 (M+H⁺)

4'-Trifluoromethyl-biphenyl-2-carboxylic acid [2-(3,5-bis-trifluoromethyl-benzyl)-1,2,3,4tetrahydroisoquinolin-6-yl]-amide
Solvent: DCE
MS (Cl): 622 (M+H⁺)

Aceticacid3-{6-[(4'-trifluoromethyl-biphenyl-2-carbonyl)-amino]-3,4-dihydro-1H-isoquinolin-2-ylmethyl}-phenyl ester
Solvent: DCE
MS (Cl): 545 (M+H⁺)

4'-Trifluoromethyl-biphenyl-2-carboxylic acid [2-(3-sulfamoyl-benzyl)-1,2,3,4-tetrahydroisoquinolin-6-yl]-amide
Solvent: DCE
MS (Cl): 566 (M+H⁺)

4'-Trifluoromethyl-biphenyl-2-carboxylic acid [2-(1H-imidazol-2-ylmethyl)-1,2,3,4-tetrahydroisoquinolin-6-yl]-amide
Solvent: 7:3 THF:DCE
59% yield
MS (Cl): 477 (M+H⁺)
¹H NMR (300 MHz, CDCl₃) δ 3.79 (s, 2H); 3.58 (s, 2H); 2.82 (m, 2H); 2.74 (m, 2H).

4'-Trifluoromethyl-biphenyl-2-carboxylic acid [2-(1-methyl-1H-pyrrol-2-ylmethyl)-1,2,3,4-tetrahydroisoquinolin-6-yl]-amide
Solvent: DCE
57% yield
MS (Cl): 490 (M+H⁺)
¹H NMR (260 MHz, CDCl₃) 63.64 (s, 3H); 3.57 (s, 2H); 3.51 (s, 2H); 2.77 (t, 2H); 2.65 (t, 2H).

4'-Trifluoromethyl-biphenyl-2-carboxylic acid [2-(1H-benzoimidazol-2-ylmethyl)-1,2,3,4-tetrahydroisoquinolin-6-yl]-amide
Solvent: DCE
83% yield
MS (Cl): 527 (M+H⁺)
¹H NMR (250 MHz, DMSO) δ 3.89 (s, 2H); 3.58 (s, 2H); 2.76 (m, 4H).

4'-Trifluoromethyl-biphenyl-2-carboxylic acid [2-(1H-imidazol4-ylmethyl)-1,2,3,4-tetrahydroisoquinolin-6-yl]-amide Solvent: DCE
66% yield
    MS (CI): 477 (M+H$^+$)
    $^1$H NMR (250 MHz, DMSO) δ 3.56 (s, 2H); 3.46 (s, 2H); 2.72 (m, 2H); 2.63 (m, 2H).
    4'-Trifluoromethyl-biphenyl-2-carboxylic acid (2-thiazol-2-ylmethyl-1,2,3,4-tetrahydroisoquinolin-6-yl)-amide
Solvent: DCE
38% yield
    MS (CI): 494 (M+H$^+$)
    $^1$H NMR (250 MHz, DMSO) δ 3.99 (s, 2H); 3.64 (s, 2H); 2.76 (s, 4H).
    4'-Trifluoromethyl-biphenyl-2-carboxylic acid [2-(3-methyl-benz[b]thiophen-2-ylmethyl)-1,2,3,4tetrahydroisoquinolin-6-yl]-amide
Solvent: DCE
    MS (CI): 557 (M+H$^+$)
    4'-Trifluoromethyl-biphenyl-2-carboxylic acid [2-(1methyl-1H-imidazol-2-ylmethyl)-1,2,3,4-tetrahydroisoquinolin-6-yl]-amide
Solvent: 7:3 THF:DCE
72% yield
    MS (CI):. 491 (M+H$^+$)
    $^1$H NMR (300 MHz, DMSO) δ 3.66 (s, 2H); 3.63 (s, 3H); 3.47 (s, 2H); 2.70 (m, 2H); 2.62 (m, 2H).
    4'-Trifluoromethyl-biphenyl-2-carboxylic acid [2-(3-methyl-3H-imidazol-4ylmethyl)-1,2,3,4tetrahydroisoquinolin-6-yl]-amide
Solvent: THF
    MS (CI): 491 (M+H$^+$)
    4'-Trifluoromethyl-biphenyl-2-carboxylic acid [2-(1H-[1,2,4]triazol-3-ylmethyl)-1,2,3,4-tetrahydroisoquinolin-6-yl]-amide
Solvent: EtOH; Temp: 70° C.
42% yield
    MS (CI): 478 (M+H$^+$)
    $^1$H NMR (250 MHz, CDCl$_3$) δ 3.87 (s, 2H); 3.63 (s, 2H); 2.79 (s, 4H).
    4'-Trifluoromethyl-biphenyl-2-carboxylic acid (2-methyl-1,2,3,4-tetrahydroisoquinolin-6-yl)-amide
Solvent: THF; 3 equiv. of aldehyde used
    MS (CI): 411 (M+H$^+$)

EXAMPLE 194

This example demonstrates how to make a compound of formula II as illustrated in Scheme 2. Numbers in parentheses with each title compound correspond to numbers in Scheme 2.

a. 2-(carboxy-5-nitro-phenyl)malonic acid dimethyl ester (2)

A solution of 2-chloro-4-nitrobenzoic acid (75 g, 372 mmol) in dimethyl malonate (900 mL) was sparged with nitrogen for 15 min. Sodium methoxide (48.3 g, 894 mmol) was added in one portion and the contents exothermed to 480° C. Fifteen minutes later, copper (I) bromide (5.4 g, 37 mmol) was added in one portion and the contents heated to 70° C. for 24 hrs. The reaction was 70% complete by nmr, the contents heated to 85° C. for 6 hrs to completely consume the 2-chloro-4-nitrobenzoic. Water (900 mL) was added to the cooled reaction followed by hexanes (900 mL). The aqueous layer was separated, toluene (900 mL) added, filtered through celite, and aqueous layer separated. Fresh toluene (1800 mL) was added to the aqueous layer and the biphasic mixture acidified with 6N aqueous HCl (90 mL). A white precipitate formed and the contents stirred for 18 hrs. The product was filtered off and dried to give a white soid (78.1 g, 70%) mp=153° C.

$^1$H NMR (CD$_3$)$_2$SO δ 78.37 (d, J=2 Hz, 1H), 8.30 (d, J=1 Hz, 2H), 5.82 (s, 1H), (3.83 (s, 6H).
$^{13}$C NMR (CD$_3$)$_2$SO δ 168.0, 167.3, 149.4, 137.1, 135.8, 132.5, 125.4, 123.7, 54.5, 53.4.
Anal. Calcd for C$_{11}$H$_{10}$NO$_8$: C, 48.49; H, 3.73; N, 4.71. Found: C, 48.27; H. 3.72; N, 4.76.

b. 2-carboxymethyl-4-nitro-benzoic acid (3)

To a solution of 2-(carboxy-5-nitro-phenyl)malonic acid dimethyl ester, (25.0 g, 84 mmol) in methanol (200 mL), sodium hydroxide (5 g, 125 mmol) in water (200 mL) was added. After 3 hrs the reaction was complete, the methanol removed under vacuum, contents cooled to 0° C. and acidified with concentrated HCl (37 mL). The aqueous layer was extracted twice with ethyl acetate (200 mL then 100 mL), the combined organic layers dried with magnesium sulfate, most of the solvent removed under vacuum, and methylene chloride (30 mL) was then added. The white solid was filtered off and dried to give 19.3 g of product as a white solid, mp=180–82° C. IR(KBr) 3080, 3055, 2983, 1707, 1611, 1585, 1516, 1491, 1424, 1358; 1298, 1237 cm$^{-1}$.
$^{13}$C NMR (CD$_3$)$_2$SO δ 172.3, 167.5, 149.2, 138.8, 137.3, 132.1, 127.2, 122.4, 39.8.
Anal. Calcd for C$_9$H$_{17}$NO$_6$: C, 48.01; H, 3.13; N, 6.22. Found: C, 47.67; H, 3.19; N, 6.31.

c. 2-(2-hydroxymethyl-5-nitro-phenyl)-ethanol (4)

A THF (60 mL) solution of 2-carboxymethyl-4-nitro-benzoic acid (3.0 g , 13.3 mmol) was treated with borane-THF complex (53.3 mL, 53.3 mmol) over 15 min at 0° C. The reaction was stirred for 18.5 hrs, quenched with THF/water (1:1, 30 mL), water (20 mL) added and the layers separated. The aqueous layer was reextracted with THF (30 mL); the combined organic phase washed with brine, dried with magnesium sulfate, and solvent removed under vacuum to give the product as a white solid (2.06 g, 78%) mp=79–81° C.
IR(KBr) 3277, 3192, 2964, 2932, 1614, 1525, 1507, 1170, 1134, 1089, 1067 cm.$^{-1}$.
$^{13}$C NMR (CD$_3$)$_2$SO δ 149.1, 146.6, 139.2, 127.8, 124.31 121.3, 61.2, 60.6, 34.9.
Anal. Calcd for C$_9$H$_{11}$NO$_4$: C, 54.82; H, 5.62; N, 7.10. Found: C, 54.54, H, 5.49; N, 7.07.

c. 2-(2-hydroxymethyl-5nitro-phenyl)-ethanol (4), alternative procedure

A mixture of 2 carboxymethyl-4-nitro-benzoic acid (13 g, 57.7 mmol), acetic anhydride (5.45 mL, 57.7 mmol) and toluene (30 mL) were heated to reflux for 5 hrs. The solvent was removed under vacuum to yield 6-nitro-isochroman-1,3-dione (compound (3a) in Scheme 2) as a yellow solid (10.51 g, 88%). Borane tetrahydrofuran complex (35.6 mL, 1M in THF) was added dropwise over 40 min to a solution of 6nitro-isochroman-1,3-dione (2 g, 9.66 mmol) in THF (40 mL) at 0° C. The contents were stirred for 18 hrs at 25° C., cooled to 0° C., quenched with methanol (30 mL), and stirred for 1 hr. The solvents were removed under vacuum, ethyl acetate (30 mL) added and the organic phase washed with 10% aqueous hydrochloric acid. The aqueous acidic layer was reextracted with ethyl acetate (30 mL), the combined organic layers dried with magnesium sulfate, and evaporated under vacuum until 2 mL of ethyl acetate remained. This solution was filtered through silica gel washing with methylene chloride (30 mL) to remove impurities. The silica gel was flushed with ethyl acetate, solvent removed under vacuum to give a solid which was slurryed in methylene chloride and filtered to afford the diol as a white solid, 1.38 g, 73%.

d. 6-nitro-1,2,3,4-tetrahydro-isoquinoline (5)

Methanesulfonyl chloride (0.9 mL, 11.63 mmol) was added dropwise over 10 min to a solution of 2-(2-hydroxymethyl-5-nitrophenyl)-ethanol (1.0 g, 5.07 mmol), triethyl amine (1.8 mL, 12.91 mmol), in methylene chloride (20 mL). TLC showed complete reaction after 30 min. $^1$H NMR (CD$_3$Cl) δ 8.17–11 (m, 2H), 7.65 (d, J=9 Hz, 1H), (s, 2H), 4.49 (t, J=6 Hz, 2H), 3.25 (t, J=6 Hz, 2H), 3.08 (s, 3H), 2.98 (s, 3H). reaction mixture was washed with 10% aqueous HCL, saturated aqueous sodium bicarbonate, and brine. The organic layer was dried with magnesium sulfate, methylene chloride removed under vacuum and chased with THF (3×100 mL). The product 1.9 g was employed directly in the next reaction without further purification. Ammonia (50 mL) was added to the dimesylate (1.9 g) in THF (30 mL) at −78° C. The contents were warmed to 24° C. for 60 hrs, ammonia distilled out, and solvent removed under vacuum to give the crude product (786 mg, 82%). Toluene was added and the solution was filtered through magnesium sulfate, and solvent removed under vacuum to yield 721 mg (75%) of an amber oil.

$^1$H NMR (CDCl$_3$) δ 7.97 (s, 1H), 7.95 (d, J=9 Hz, 1H), 7.15 (d, J=9 Hz, 1H), 4.07 (s, 2H), 3.15 (t, J=6 Hz, 2H), 2.89 (t, J=6 Hz, 2H), 1.98 (bs, 1H).

e. 6-nitro-3,4-dihydro-1H-isoquinoline2-carboxylic acid tert-butyl ester (6)

To a solution of 6-nitro-1,2,3,4-tetrahydroisoquinoline (840 mg, 4.71 mmol) in methylene chloride (17 mL) containing triethylamine (0.72 mL), 5.17 mmol) was added BOC-anhydride (1.44 mL, 6.26 mmol). Saturated aqueous sodium bicarbonate was added 5 hr later, the phases separated, organic layer dried with magnesium sulfate, and solvent removed under vacuum to give the product as a pale white solid (1.2 g, 92%). mp=138–41° C.

IR(KBr) 3056, 3018, 2982, 2935, 1734, 1684, 1612, 1522, 1399, 1236 cm$^{-1}$. $^1$H NMR (CDCl$_3$) δ 8.04 (t, J=5 Hz, 1H), 8.01 (s, 1H), 7.26 (t, J=5 Hz, 1H), (s, 2H), 3.68 (t, J=6 Hz, 2H), 2.93 (t, J=6 Hz, 2H), 1.49 (s, 9H).

f. 6-amino-3,4-hydro-1H-isoquinoline-2-carboxylic acid tert-butyl ester (7)

The 6-nitro-3,4dihydro-1H-isoquinoline-2-carboxylic acid tert-utyl ester (82 mg, 0.29 mmol) in THF (2 mL) was hydrogenated with 5%Pt-C (50% water wet, 10 mg) at 50 psi for 5 hrs. The catalyst was filter off, solvent removed under vacuum and chromatographed on silica with ethyl acetate / hexanes to give 42 mg (57%) of the product.

IR(KBr) 3005, 2975, 2928, 1685, 1627, 1509, 1423, 1365, 1166 cm$^{-1}$.

$^1$H NMR (CDCl$_3$) δ 6.90 (d, J=6 Hz, 1H), 6.56 (d, J=6 Hz, 1H), 6.48 (s, 1H), 4.47 (s, 2H), 3.60 (m, J=6 Hz, 4H), 2.73 (t, J=6 Hz, 2H), 1.49 (s, 9H).

The product made as in Example 194 above can be reacted with 4'-trfluoromethyl-biphenyl-2-carboxylic acid as disclosed in Example 1 to afford the N-blocked compound II, then deblocked to yield compound II.

EXAMPLE 195

This example demonstrates how to make compound II as shown in Scheme 3. Numbers in parentheses correspond to those in Scheme 3.

a. 4'-trifluoromethyl-biphenyl-2-carbonyl chloride

A solution of 4(trifluoromethyl)-2-biphenylcarboxylic acid (9.08 g, 34 mmol), thionyl chloride (12 mL) and dimethylformamide (0.05 mL) was heated to reflux for 2 hrs. The reaction was complete by NMR. Thionyl chloride was distilled by displacing with toluene (56 mL). Solvent was removed under vacuum to give the acid chloride as a white solid (9.46 g, 97%).

$^1$H NMR (CDCl$_3$) δ 8.12 (dd, J=1 Hz, J=8 Hz, 1H), 7.70–7.37 (m, 7H). $^{13}$C NMR CD$_3$Cl δ (CO) 168.

b. 4'-trifluoromethyl-biphenyl-2-carboxylic acid-[3-(2-hydroxy-ethyl)-4-hydroxymethyl-phenyl]-amide (10)

Pt-C (50% water wet, 200 mg) was added to a THF (40 mL) solution of 2-(2 hydroxymethly-5-nitro-phenyl)-ethanol (1.0 g, 5 mmol) and the reaction hydrogenated at 50 psi for 2 hrs. NMR showed complete reaction to form 2-(5-amino-2-hydroxymethyl-phenyl)-ethanol (compound (9) in Scheme 3);

$^1$H NMR (CD$_3$Cl) δ 7.08 (d, J=2 Hz, 1H), 6.54–6.50 (m, 2H), 4.51 (s, 2H), 3.82 (t, J=6 Hz, 2H), 3.80–2.95 (bs, 4H), 2.84 (t, J=6 Hz, 2H).

The catalyst was filtered off, triethylamine (1.4 mL, 10 mmol) added, followed by dropwise addition of a THF (10 mL) solution of the 4'-trifluoromethyl-biphenyl-2-carbonyl chloride (1.44 g, 5 mmol) over 1 hr. The contents were stirred for 24 hrs, the solvent removed under vacuum, and ethyl acetate (40 mL) added. The organic phase was washed with water (2×40 mL), dried with magnesium sulfate, solvent removed under vacuum, and chased with toluene (3×40 mL). Upon removal of the solvent 2.11 g a white solid was obtained which was repulsed in methylene chloride (21 mL) for 18 hrs, the product filtered off, and dried to give the title product as a white solid 1.71 g (81%).

$^1$H NMR (CD$_3$)$_2$SO δ 10.22 (s, 1H), 7.73 (d, J=8 Hz, 2H), 7.62-28 (m, 8H), 7.20 (d, J=8 Hz, 1H), 4.96 (bs, 1H), 4.69 (bs, 1H), 4.43 (s, 2H), 3.51 (t, J=7 Hz, 2H), 2.67 (t, J=7 Hz, 2H).

IR(KBr) 3264, 3232, 31278, 3124, 3106, 2956, 2928, 1649, 1613, 1533, 1328, 1129 cm$^{-1}$.

$^{13}$C NMR (CD$_3$)$_2$SO δ (amide CO) 167.7, aliphatic carbons 62.3, 61.1, 36.0.

Anal. Calcd for C$_{23}$F$_3$H$_{20}$NO$_3$: C, 66.50; H, 4.85; N, 3.37. Found: C, 66.29; H, 4.79; N, 3.27.

c. 4'-trifluoromethyl-biphenyl-2-carboxylic acid (1,2,3,4-tetrahydroisoquinolin-6-yl)-amide (compound 11).

Methanesulfonyl chloride (0.085 mL) was added to a 0° C. solution of 4'-trifluoromethyl-biphenyl-2-carboxylic acid-[3-(2-hydroxy-ethyl)-4-hydroxylmethyl-phenyl]-amide (214 mg, 0.51 mmol) and triethylamine (0.18 mL) in THF (8.5 mL). TLC showed complete reaction after 30 min. The contents were cooled to −78° C. and ammonia was added and the contents stirred for 18 hrs at 250° C. The solvents were removed under vacuum, methylene chloride (10 mL) and aqueous 1N aqueous HCl added and the contents stirred for 1 hr. The phases were separated and the aqueous phase made alkaline with aqueous sodium hydroxide to a pH of 12. The organic phase was extracted with methylene chloride (4×10 mL), solvent removed under vacuum to give a white solid 108 mg which was chromatographed on silica eluting with 5% methanol/methylene chloride with 0.5% ammonium hydroxide. The product was obtained as a white solid (40 mg, 20%).

$^1$H NMR (CDCl$_3$) δ 7.76–6.83 (m, 11H), 3.89 (s, 2H), 3.52 (d, J=7 Hz, 0.5H), 3.04 (t, J=6 Hz, 2H), 2.74 (m, 0.5H), 2.66 (t, J=7 Hz, 2H), 2.27 (s, 1H).

$^{13}$C NMR CD$_3$Cl δ (aliphatic carbons only) 47.8, 43.6, 29.1.

Examples 196–197 demonstrate how to make compounds according to the invention as illustrated in Scheme 3.

EXAMPLE 196

4'-trifluoromethyl-biphenyl-2-carboxylic acid (2-benzyl-1,2,3,4-tetrahydroisoquinolin-6yl)-amide Methanesulfonyl chloride (0.041 mL) was added to a 0° C. solution of 4'-trifluoromethyl-biphenyl-2-carboxylic acid-[3-(2-hydroxy-ethyl)-4-hydroxymethyl-phenyl]-amide (100 mg, 0.24 mmol) and triethylamine (0.084 mL) in THF (2 mL). TLC showed complete reaction after 30 min. Benzylamine (0.132 mL) was added and the contents stirred for 18 hrs at 25° C. and 60 hrs at 50° C. The solvent was removed under vacuum, the residue dissolved in methylene chloride (15 mL), washed with pH9 buffer, phases separated, and the organic phase dried with magnesium sulfate. Removal of the solvent under vacuum gave the crude product as a white solid (204 mg), which was repulsed in CDCl$_3$ filtered off and dried to give the product as a white solid (46 mg, 39%). mp=230–32° C.

$^1$H NMR (CD$_3$)$_2$SO δ 7.73 (d, J=8 Hz, 2H), 7.60-23 (m, 12H), 7.17 (d, J=8Hz, 1H), 6.87 (d, J=8 Hz, 1H), 3.60 (s, 2H), 3.43 (s, 2H), 2.71 (m, 2H), 2.62 (m, 2H).

Anal. for C$_{30}$F$_3$H$_{25}$N$_2$O: C, 74.06; H, 5.18; N, 5.76. Found: C, 74.08; H, 5.38; N, 5.76.

EXAMPLE 197

4'-trifluoromethyl-biphenyl-2-carboxylic acid (2-allyl-1,2,3,4-tetrahydroisoquinolin-6yl)-amide Methanesulfonyl chloride (0.041 mL, 0.53 mmol) was added dropwise to a THF (2 mL) solution of triethylamine (0.084 mL, 0.60 mmol) and 4'-trifluoromethyl-biphenyl-2-carboxylic acid-[3-(2-hydroxy-ethyl)-4-hydroxylmethyl-phenyl]-amide (0.1 g, 0.24 mmol) at –20° C. Fifteen minutes after the addition was complete allylamine (0.09 mL, 1.2 mmol) was added, the contents stirred at 25° C. for 18 hrs and then 70 hrs at 60° C. The solvent was removed under vacuum, methylene chloride (10 mL) added and organic phase washed with pH12 water (10 mL). The organic solvent was removed under vacuum to afford 281 mg of crude product. This material was chromatographed on silica eluting with 10%methanol/methylene chloride to afford the product as a white solid (91 mg, 87%).

$^1$H NMR (CDCl$_3$) δ 7.80 (d, J=8 Hz, 1H), 7.68 (d, J=8 Hz, 2H), 7.60-7.42 (m, 5H), 6.93-6.83 (m, 3H), 6.00-5.86 (m, 1H), 5.27–5.17 (m, 2H), 3.55 (s, 2H), 3.15 (d, J=7 Hz, 2H), 2.83 (t, J=6 Hz, 2H), 2.69 (t, J=6 Hz, 2H), 1.66 (bs, 1H).

$^{13}$C NMR CD$_3$Cl δ (aliphatic carbons only) 61.4, 55.6, 50.3, 29.1.

What is claimed is:

1. A compound of formula I

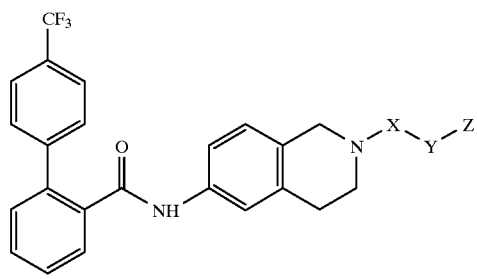

wherein

X is CH$_2$, CO, CS, or SO$_2$;

Y is selected from:
 a direct link,
 aliphatic hydrocarbyiene radicals having up to 20 carbon atoms, which radical may be mono-substituted by hydroxy, (C$_1$–C$_{10}$)alkoxy, (C$_1$–C$_{10}$)acyl, (C$_1$–C$_{10}$)acyloxy, or (C$_6$–C$_{10}$)aryl,
 NH, and O, provided that if X is CH$_2$, Y is a direct link;

Z is selected from the following groups:

(1) H, halo, cyano,
(2) hydroxy, (C$_1$–C$_{10}$)alkoxy, (C$_1$–C$_{10}$)alkylthio, (C$_1$–C$_{10}$)acyl, thiophenylcarbonyl, (C$_1$–C$_{10}$)alkoxycarbonyl,
(3) (C$_1$–C$_{10}$)alkylamino, di(C$_1$–C$_{10}$)alkylamino, (C$_6$–C$_{10}$)aryl (C$_1$–C$_{10}$)alkylamino, provided that Y is not O or NH,
(4) unsubstituted vinyl, (C$_6$–C$_{10}$)aryl, (C$_3$–C$_8$)cycloalkyl and fused benz derivatives thereof, (C$_7$–C$_{10}$)polycycloalkyl, (C$_4$–C$_8$)cycloalkenyl, (C$_7$–C$_{10}$)polycycloalkenyl,
(5) (C$_6$–C$_{10}$)aryloxy, (C$_6$–C$_{10}$)arylthio, (C$_6$–C$_{10}$)aryl (C$_1$–C$_{10}$)alkoxy, (C$_6$–C$_{10}$)aryl(C$_1$–C$_{10}$)alkylthio, (C$_3$–C$_8$)cycloalkyloxy, (C$_4$–C$_8$)cycloalkenyloxy,
(6) heterocycle selected from the group consisting of monocyclic radicals and fused polycyclic radicals, wherein said radicals contain a total of from 5 to 14 ring atoms, wherein said radicals contain a total of from 1 to 4 ring heteroatoms independently selected from oxygen, nitrogen, and sulfur, and wherein the individual rings of said radicals may be independently saturated, partially unsaturated, or aromatic, provided that if X is CH$_2$, Z is H or is selected from groups (4) and (6), wherein, when Z contains one or more rings, said rings may each independently bear 0 to 4 substituents independently selected from halo, hydroxy, cyano, nitro, oxo, thioxy, aminosulfonyl, phenyl, phenoxy, phenylthio, halophenylthio, benzyl, benzyloxy, (C$_1$–C$_{10}$)alkyl,(C$_1$–C$_{10}$)alkoxy, (C$_1$–C$_{10}$)alkoxycarbonyl,(C$_1$–C$_{10}$)alkylthio, (C$_1$–C$_{10}$)alkylamino, (C$_1$–C$_{10}$)alkylaminocarbonyl, di(C$_1$–C$_{10}$)alkylamino, di(C$_1$–C$_{10}$)alkylaminocarbonyl, di(C$_1$–C$_{10}$)alkylamino, (C$_1$–C$_{10}$)alkoxy, (C$_1$–C$_3$)perfluoroalkyl, (C$_1$–C$_3$)perfluoroalkoxy, (C$_1$–C$_{10}$)acyl, (C$_1$–C$_{10}$)acyloxy, (C$_1$–C$_{10}$)acyloxy(C$_1$–C$_{10}$)alkyl, and pyrrolidinyl;

and pharmaceutically acceptable salts thereof.

2. A compound as defined in claim 1, and pharmaceutically acceptable salts thereof, wherein:

X is CH$_2$, CO, or SO$_2$;

Y is selected from:
 a direct link, NH,
 (C$_1$–C$_{10}$)alkylene and (C$_2$–C$_{10}$)alkenylene, either of which maybe substituted with phenyl, provided that if X is CH$_2$, Y is a direct link, Z is selected from the following groups:
(1) H,
(2) (C$_1$–C$_{10}$)alkoxy, (C$_1$–C$_{10}$)alkylthio,
(3) (C$_1$–C$_{10}$)alkylamino, di(C$_1$–C$_{10}$)alkylamino, (C$_6$–C$_{10}$)aryl, (C$_1$–C$_{10}$)alkylamino, provided that Y is not NH,
(4) unsubstituted vinyl, (C$_6$–C$_{10}$)aryl, (C$_3$–C$_8$)cycloalkyl, (C$_4$–C$_8$)cycloalkenyl,
(5) (C$_6$–C$_{10}$)aryloxy,
(6) heterocycle selected from the group consisting of five- and six-membered heterocyclic radicals, which may be saturated, partially unsaturated, or aromatic, and the fused benz derivatives thereof, wherein said radicals may contain a total of from 1 to 3 ring heteroatoms independently selected from oxygen, nitrogen, and sulfur, wherein, when Z contains one or more rings, said rings may each independently bear 0 to 3 substituents independently selected from halo, hydroxy, nitro, (C$_1$–C$_6$)alkyl, (C$_1$–C$_6$)alkoxy, di(C$_1$–C$_6$)alkylaminocarbonyl, (C$_1$–C$_3$)perfluoroalkoxy, (C$_1$–C$_{10}$)acyl, and (C$_1$–C$_{10}$)acyloxy.

3. A compound as defined in claim 2, and pharmaceutically acceptable salts thereof, wherein X is methylene, Y is a direct link, and Z is selected from $(C_6-C_{10})$aryl, $(C_3-C_8)$ cycloalkyl, and $(C_4-C_8)$cycloalkenyl each of which may bear 0 to 3 of the said independent substituents.

4. A compound as defined in claim 2, and pharmaceutically acceptable salts thereof, wherein X is methylene or CO, Y is a direct link, and Z is heterocycle selected from thiophenyl, pyrrolidinyl, pyrrolyl, furanyl, thiazolyl, isoxazolyl, imidazolyl, 1,2,4-triazolyl, pyridyl, pyrimidinyl, and the fused bicyclic (ortho) benz derivatives thereof, each of which may bear 0 to 3 of the said independent substituents.

5. A compound as defined in claim 2, and pharmaceutically acceptable salts thereof,
wherein
X is $CH_2$ or CO;
Y is a direct link;
Z is H, unsubstituted vinyl, phenyl, imidazolyl, thiazolyl, thiophenyl, 1,2,4-triazolyl, pyridinyl, and pyrimidinyl.

6. A compound as defined in claim 5, wherein X is CO.
7. A compound as defined in claim 5, wherein X is $CH_2$.
8. A compound as defined in claim 1, wherein the linking group formed by the ring nitrogen of the 1,2,3,4-tetrahydroisoquinoline ring shown in formula I taken together with the group in -XYZ which links the said XYZ moiety to the said ring nitrogen is selected from:

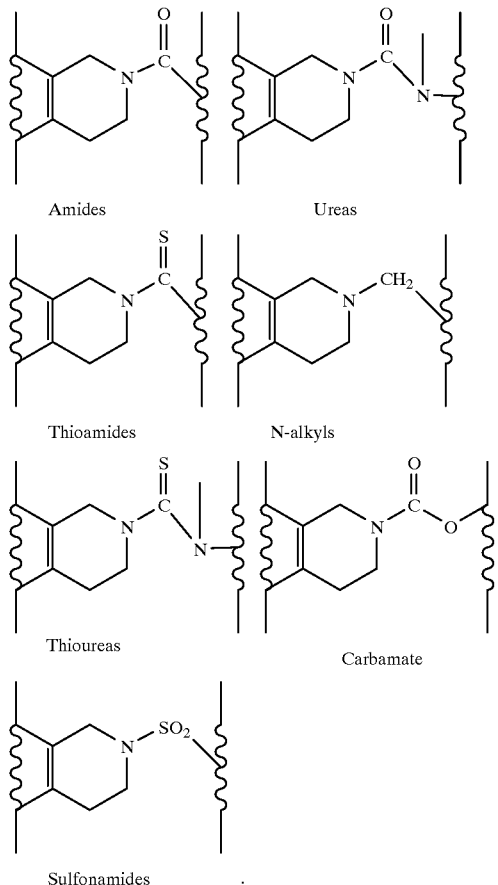

Amides   Ureas

Thioamides   N-alkyls

Thioureas   Carbamate

Sulfonamides

9. A compound as defined in claim 8, wherein said linking group is an amide.

10. A compound as defined in claim 9, selected from the group consisting of:

4'-Trifluoromethyl-biphenyl-2-carboxylic acid (2-phenyl-acetyl-1,2,3,4tetrahydroisoquinolin-6-yl)-amide, 4'-Trifluoromethyl-biphenyl-2-carboxylic acid (2-phenoxymethyl-1,2,3,4tetrahydro- isoquinolin-6-yl)-amide, 4'-Trifluoromethyl-biphenyl-2-carboxylic acid (2-pentanoyl-1,2,3,4-tetrahydroisoquinolin-6-yl)-amide, 4'-Trifluoromethyl-biphenyl-2-carboxylic acid (2-cyclobutane-carbonyl-1,2,3,4-tetrahydro-isoquinolin-6yl)-amide, 4'-Trifluoromethyl-biphenyl-2-carboxylic acid [2-(thiophen-2-yl-acetyl)-1,2,3,4-tetrahydro-isoquinolin-6-yl]-amide, 4'-Trifluoromethyl-biphenyl-2-carboxylic acid (2-butyryl-1,2,3,4-tetrahydroisoquinolin-6yl)-amide, 4'-Trifluoromethyl-biphenyl-2-carboxylic acid (2-ethoxy-acetyl-1,2,3,4-tetrahydro-isoquinolin-6-yl)-amide, 4'-Trifluoromethyl-biphenyl-2-carboxylic acid{2-[(4-fluoro-phenyl)-acetyl]-1,2,3,4-tetrahydroisoquinolin-6-yl}-amide, 4'-Trifluoromethyl-biphenyl-2-carboxylic acid [2-(3-methyl-butyl)-,1,2,3,4tetrahydro-isoquinolin-6-yl]-amide, 4'-Trifluoromethyl-biphenyl-2-carboxylic acid (2-but-3-enoyl-1,2,3,4-tetrahydroisoquinolin-6-yl)-amide, 4'-Trifluoromethyl-biphenyl-2-carboxylic acid (2-methoxy-acetyl-1,2,3,4-tetrahydroisoquinolin-6-yl)-amide, 4'-Trifluoromethyl-biphenyl-2-carboxylic acid (2-ethylthio -1,2,3,4-tetrahydroisoquinolin-6-yl)-amide, 4'-Trifluoromethyl-biphenyl-2carboxylic acid[2-(6diethyl-carbamoyl-cyclohexyl-3-enecarbonyl)-1,2,3,4-tetrahydroisoquinolin-6-yl]-mide, 4'-Trifluoromethyl-biphenyl-2carboxylic acid[2-(cyclopent-1-enyl-acetyl)-1,2,3,4-tetrahydroisoquinolin-6-yl ]-amide, 4'-Trifluoromethyl-biphenyl-2-carboxylic acid (2-hex-3enoyl-1,2,3,4tetrahydroisoquinolin4-yl)-amide, 4'-Trifluoromethyl-biphenyl-2-carboxylic acid [2-(tetrahydrofuran-3-carbonyl)-1,2,3,4-tetrahydroisoquinolin-6-yl]-amide, 4'-Trifluoromethyl-biphenyl-2-carboxylic acid [2-(thiophen-2-yl-acetyl)-1,2,3,4-tetrahydro-isoquinolin-6-yl]-amide, and 4'-Trifluoromethyl-biphenyl-2-carboxylic acid [2-(pyridine-2-carbonyl)-1,2,3,4-tetrahydro-isoquinolin-6-yl]-amide.

11. A compound as defined in claim 8, wherein said linking group is a urea.

12. A compound as defined in claim 11, selected from the group consisting of:

6-[(4'-Trifluoromethyl-biphenyl-2-carbonyl)-amino]4-dihydro-1H-isoquinoline-2-carboxylic acid phenylamide, 6-[(4'-Trifluoromethyl-biphenyl-2-carbonyl)-amino]-3,4-dihydro-1H-isoquinoline-2-carboxylic acid hexylamide, 6-[(4'-Trifluoromethyl-biphenyl-2-carbonyl)-amino]-3,4di-hydro-1H-isoquinoline-2-carboxylic acid benzylamide, 6-[(4'-Trifluoromethyl-biphenyl-2-carbonyl)-aino]-,4dihydro-1H-isoquinoline-2-carboxylic acid [(R)-1-phenyI-ethyl]-amide, and 6-[(4'-Trifluoromethyl-biphenyl-2-carbonyl)-amino]-3,4-dihydro-1H-isoquinoline-2-carboxylic acid pyridin-2-ylamide.

13. A compound as defined in claim 8, wherein said linking group is a sulfonamide.

14. A compound as defined in claim 13, selected from the group consisting of:

4'-Trifluoromethyl-biphenyl-2-carboxylic acid [2-(propane-2-sulfonyl)-1,2,3,4-tetrahydro-isoquinolin-6-yl]-amide, 4'-Trifluoromethyl-biphenyl-2-carboxylic acid (2-dimethylsulfamoyl-1,2,3,4-tetrahydro-isoquinolin-6-yl)-amide, and 4'-Trifluoromethyl-biphenyl-2-carboxylic acid [2-(2-trifluoromethoxy-enzenesulfonyl)-1,2,3,4tetrahydroisoquinolin-6-yl]-amide.

15. A compound as defined in claim 8, wherein said linking group is a thiourea.

16. A compound as defined in claim 15, which is 4'-Trifluoromethyl-biphenyl-2-carboxylic acid (2-cyclopropylthiocarbamoyl-1,2,3,4-tetrahydroisoquinolin-6-yl)-amide.

17. A compound as defined in claim 8, wherein said linking group is a N-alkyl.

18. A compound as defined in claim 17, selected from the group consisting of:

4'-Trifluoromethyl-biphenyl-2-carboxylic acid [2-(2,6,6-trimethyl-cyclohexyl-2-enylmethyl)-1,2,3,4-tetrahydroisoquinoline-6-yl]-amide, 4'-Trifluoromethyl-biphenyl-2-carboxylic acid [2-(2,4dichloro-benzyl)-1,2,3,4-tetrahydro-isoquinolin-6-yl]-amide, 4'-Trifluoromethyl-biphenyl-2-carboxylic acid [2-(1,5a,6,9,9a,9b-hexahydro-4H-dibenzofuran-4a-ylmethyl)-1,2,3,4-tetrahydroisoquinolin-6-yl]-amide, 4'-Trifluoromethyl-biphenyl-2-carboxylic acid (2-thiophen-2-ylmethyl-1,2,3,4-tetrahydro-isoquinolin-6-yl)-amide, 4'-Trifluoromethyl-biphenyl-2-carboxylic acid [2-(1H-pyrrolyl-2-ylmethyl)-1,2,3,4-tetrahydro-isoquinolin-6-yl]-amide, 4'-Trifluoromethyl-biphenyl-2-carboxylic acid (2-furan-2-ylmethyl-1,2,3,4-tetrahydro-isoquinolin-6-yl)-amide, Acetic acid5-{6-[(4'-trifluoromethyl-biphenyl-2carbonyl)-amino]-3,4-dihydro-1H-isoquinolin-2-ylmethyl}-furan-2-ylmethyl ester, 4'-Trifluoromethyl-biphenyl-2-carboxylic acid (2-thiophen-3-ylmethyl-1,2,3,4-tetrahydro-isoquinolin-6-yl)-amide, 4'-Trifluoromethyl-biphenyl-2-carboxylic acid [2-(2,5dimethoxy-tetrahydrofuran-3-ylmethyl)-1,2,3,4tetrahydro-isoquinolin-6-yl]-amide, 4'-Trifluoromethyl-biphenyl-2-carboxylic acid (2-benzyl-1,2,3,4-tetrahydroisoquinoline-6-yl)-amide, 4'-Trifluoromethyl-biphenyl-2-carboxylic acid (2-pyridin-2-ylmethyl-1,2,3,4-tetrahydro-isoquinolin-6-yl)-amide, 4'-Trifluoromethyl-biphenyl-2-carboxylic acid (2-quinolin-2-ylmethyl-1,2,3,4-tetrahydro-isoquinolin-6-yl)-amide, 4'-Trifluoromethyl-biphenyl-2-carboxylic acid [2-(3-chloro-benzyl)-1,2,3,4-tetrahydro-isoquinolin-6-yl]-amide, 4'-Trifluoromethyl-biphenyl-2-carboxylic acid (2-pyrimidin-2-ylmethyl-1,2,3,4-tetrahydro-isoquinolin-6-yl)-amide, 4'-Trifluoromethyl-biphenyl-2-carboxylic acid [2-(3-nitro-benzyl-1,2,3,4-tetrahydroisoquinolin-6-yl]-amide, 4'-Trifluoromethyl-biphenyl-2-carboxylic acid[2-(1H-imidazol-2-ylmethyl)-1,2,3,4-tetrahydroisoquinolin-6yl]-amide, 4'-Trifluoromethyl-biphenyl-2-carboxylic acid [2-(1-methyl-pyrrolyl-2-ylmethyl)-1,2,3,4-tetrahydroisoquinolin-6-yl]-amide, 4'-Trifluoromethyl-biphenyl-2-carboxylic acid [2-(1H-benzoimidazol-2-ylmethyl)-1,2,3,4-tetrahydroisoquinolin-6-yl]-amide, 4'-Trifluoromethyl-biphenyl-2-carboxylic acid (2-thiazol-2-ylmethyl-1,2,3,4-tetrahydroisoquinolin-6-yl)-amide, 4'-Trifluoromethyl-biphenyl-2-carboxylic acid [2-(1-methyl-imidazol-2-ylmethyl)-1,2,3,4-tetrahydroisoquinolin-6-yl]-amide, 4'-Trifluoromethyl-biphenyl-2-carboxylic acid [2-(1H-[1,2,4]thiazolylmethyl)-1,2,3,4-tetrahydroisoquinolin-6-yl]-amide, and 4'-trifluoromethyl-biphenyl-2-carboxylic acid [(2-allyl)-1,2,3,4-tetrahydroisoquinoline-6-yl]-amide.

19. A compound as defined in claim 8, wherein said linking group is a carbamate.

20. A compound as defined in claim 19, which is 6-[(4'-Trifluoromethyl-biphenyl-2-carbonyl)-amino]-3,4-dihydro-1H-isoquinoline-2-carboxylic acid tertbutyl ester.

21. A compound as defined in claim 8, wherein said linking group is a thioamide.

22. A compound as defined in claim 8, selected from the group consisting of:

4'-Trifluoromethyl-biphenyl-2-carboxylic acid [2-(thiophen-2-yl-acetyl)-1,2,3,4-tetrahydroisoquinolin-6-yl]-amide, 6[(4-Trifluoromethylphenyl-2-carbonyl)-amino]-3,4dihydro-1H-isoquinoline-2-carboxylic acid ([R]-1-phenyl-ethyl)-amide, 4'-Trifluoromethyl-biphenyl-2-carboxylic acid (2-pyridin-2-ylmethyl-1,2,3,4-tetrahydroisoquinolin-6-yl)-amide, 4'-Trifluoromethyl-biphenyl-2-carboxylic acid [2-(1H-imidazol-2-ylmethyl)-1,2,3,4-tetrahydroisoquinolin-6-yl]-amide, 4'-Trifluoromethyl-biphenyl-2-carboxylic acid (2-thiazol-2-ylmethyl-1,2,3,4-tetrahydroisoquinolin-6-yl)-amide, and 4'-Trifluoromethyl-biphenyl-2-carboxylic acid [2-(1H-[1,2,4]triazol-3-ylmethyl)-1,2,3,4-tetrahydrolsoquinolin-6-yl)]-amide.

23. A compound as defined in claim 22, which is 4-Trifluoromethyl-biphenyl-2-carboxylic acid [2-(thiophen-2-yl-acetyl)-1,2,3,4-tetrahydroisoquinolin-6yl]-amide.

24. A compound as defined in claim 22, which is 6-[(4'-Trifluoromethyl-biphenyl-2-carbonyl)-amino]-3,4dihydro-1H-4-isoquinoline-2-carboxylic acid (1-phenyl ethyl)-amide.

25. A compound as defined in claim 22, which is 4'-Trifluoromethyl-biphenyl-2-carboxylic acid (2-pyridin-2-ylmethyl-1,2,3,4-tetrahydroisoquinolin-6-yl)-amide.

26. A compound as defined in claim 22, which is 4'-Trifluoromethyl-biphenyl-2-carboxylic acid [2-(1H-imidazol-2-ylmethyl)-1,2,3,4-tetrahydroisoquinolin-6-yl]-amide.

27. A compound as defined in claim 22, which is 4'-Trifluoromethyl-biphenyl-2-carboxylic acid (2-thiazol-2-ylmethyl-1,2,3,4-tetrahydroisoquinolin-6-yl)-amide.

28. A compound as defined in claim 22, which is 4'-Trifluoromethyl-biphenyl-2-carboxylic acid [2-(1H-[1,2,4]-triazol3-ylmethyl)-1,2,3,4tetrahydroisoquinolin-6-yl]-amide.

29. A pharmaceutical composition comprising a compound of formula I as defined in claim 1, and a pharmaceutically acceptable carrier.

30. A composition as defined in claim 29, further comprising an additional lipid-lowering agent.

31. A method of treating a condition selected from atherosclerosis, pancreatitis, obesity, hypercholesteremia, hypertriglyceridemia, hyperlipidemia, and diabetes, comprising administering to a mammal in need of such treatment an amount of a compound of formula I as defined in claim 1 sufficient to decrease the secretion of apolipoprotein B.

32. A method as defined in claim 31, wherein said condition is selected from atherosclerosis, pancreatitis, obesity, and diabetes.

33. A method as defined in claim 32, wherein said condition is atherosclerosis.

34. A method of decreasing apoB secretion in a mammal, comprising administering to said mammal an apoB secretion decreasing amount of a compound of formula I as defined in claim 1.

35. A compound which is selected from:

4'-trifluoromethyl-biphenyl-2-carboxylic acid (1,2,3,4-tetrahydroisoquinolin-6-yl)-amide, 4'-trifluoromethyl-biphenyl-2-carboxylic acid-[3-(2-hydroxy-yl)hydroxylmethyl-phenyl]-amide, 2-(2-hydroxymethyl-5-nitro-phenyl)-ethanol, 6-nitro-3,4-dihydro-1H-isoquinoline-2-carboxylic acid tert-butyl ester, and 2-(5-amino-2-hydroxymethyl-phenyl)-ethanol.

36. A compound as defined in claim 35, selected from:

4'-trifluoromethyl-biphenyl-2-carboxylic acid (1,2,3,4-tetrahydroisoquinolin-6-yl)-amide and 4'-trifluoromethyl-biphenyl-2-carboxylic acid-[3-(2-hydroxy-ethyl)-4-hydroxylmethylphenyl]-amide.

* * * * *